(12) United States Patent
Tscholl et al.

(10) Patent No.: US 10,702,214 B2
(45) Date of Patent: Jul. 7, 2020

(54) METHOD AND SYSTEM FOR MONITORING A PATIENT'S MEDICAL CONDITION

(71) Applicant: Universität Zürich, Zürich (CH)

(72) Inventors: David Tscholl, Zurich (CH); Christoph Nothiger, Kilchberg (CH); Patrick Neubauer, Vienna (AT)

(73) Assignee: UNIVERSITÄT ZÜRICH, Zürich (CH)

( * ) Notice: Subject to any disclaimer, the term of this patent is extended or adjusted under 35 U.S.C. 154(b) by 43 days.

(21) Appl. No.: 15/816,749

(22) Filed: Nov. 17, 2017

(65) Prior Publication Data

US 2018/0103916 A1 Apr. 19, 2018

Related U.S. Application Data

(63) Continuation of application No. PCT/EP2016/060931, filed on May 14, 2016.

(30) Foreign Application Priority Data

May 21, 2015 (EP) ................................ 20150168778

(51) Int. Cl.
*A61B 5/00* (2006.01)
*G16H 40/63* (2018.01)
(Continued)

(52) U.S. Cl.
CPC ............ *A61B 5/745* (2013.01); *A61B 5/0006* (2013.01); *A61B 5/744* (2013.01); *A61B 5/7425* (2013.01);
(Continued)

(58) Field of Classification Search
CPC ..... A61B 5/745; A61B 5/0006; A61B 5/7425; A61B 5/744; A61B 5/0205; A61B 5/7435;
(Continued)

(56) References Cited

U.S. PATENT DOCUMENTS 6,032,119 A 2/2000 Jensen et al.
2006/0241712 A1* 10/2006 Cates ................. A61N 1/37211
607/30

(Continued)

FOREIGN PATENT DOCUMENTS

WO 2012159190 A1 11/2012

OTHER PUBLICATIONS

International Search Report and Written Opinion for International Application PCT/EP2016/060931, dated Jul. 29, 2016, 10 pages.

*Primary Examiner* — Phuc N Doan
(74) *Attorney, Agent, or Firm* — Brake Hughes Bellermann LLP

(57) ABSTRACT

A method for monitoring and visualizing a patient's medical condition, wherein a graphical representation of the patient comprising a body having at least a torso and a head, as well as particularly two legs and two arms, is displayed using a display device, wherein said displayed graphical representation comprises at least one region which is allocated to at least one or several provided (e.g. measured and/or determined) patient monitoring quantities, and wherein the appearance of the at least one region is altered in real-time when the at least one patient monitoring quantity to which said at least one region is allocated changes.

9 Claims, 31 Drawing Sheets

(51) Int. Cl.
*G16H 10/60* (2018.01)
*A61B 5/0205* (2006.01)

(52) U.S. Cl.
CPC ............. *G16H 10/60* (2018.01); *G16H 40/63* (2018.01); *A61B 5/0205* (2013.01); *A61B 5/7435* (2013.01)

(58) Field of Classification Search
CPC ........ A61B 5/743; G16H 10/60; G16H 40/63; G06F 19/30; G06F 19/32; G06F 19/34; G06Q 50/22; G06Q 50/24
See application file for complete search history.

(56) References Cited

U.S. PATENT DOCUMENTS

| | | | |
|---|---|---|---|
| 2007/0027368 A1 | 2/2007 | Collins et al. | |
| 2007/0031018 A1* | 2/2007 | Camus | A61B 6/481 382/130 |
| 2007/0050715 A1* | 3/2007 | Behar | A61B 5/0002 715/706 |
| 2011/0172564 A1* | 7/2011 | Drew | A61B 5/061 600/587 |
| 2013/0011819 A1* | 1/2013 | Horseman | A61B 5/6887 434/257 |
| 2013/0066652 A1* | 3/2013 | Heywood | A61B 5/0002 705/3 |
| 2013/0253348 A1* | 9/2013 | Tremper | A61B 5/02055 600/508 |
| 2014/0354637 A1* | 12/2014 | Reiner | G06T 17/10 345/420 |
| 2015/0097701 A1* | 4/2015 | Al-Ali | A61B 5/0002 340/870.07 |
| 2015/0173697 A1* | 6/2015 | Parks | A61B 5/14542 600/301 |
| 2015/0228254 A1* | 8/2015 | Olson | G06T 11/00 345/592 |
| 2015/0283389 A1* | 10/2015 | Stone | A61N 1/0529 607/45 |

\* cited by examiner

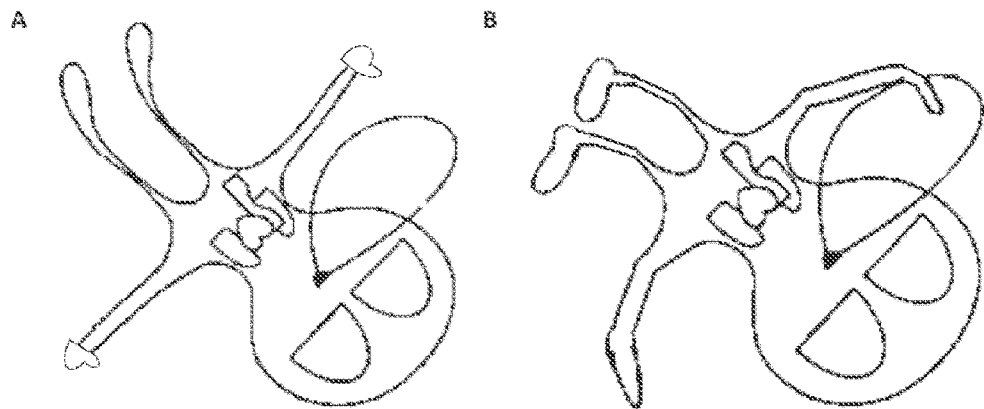
FIG. 44
Fig. 45
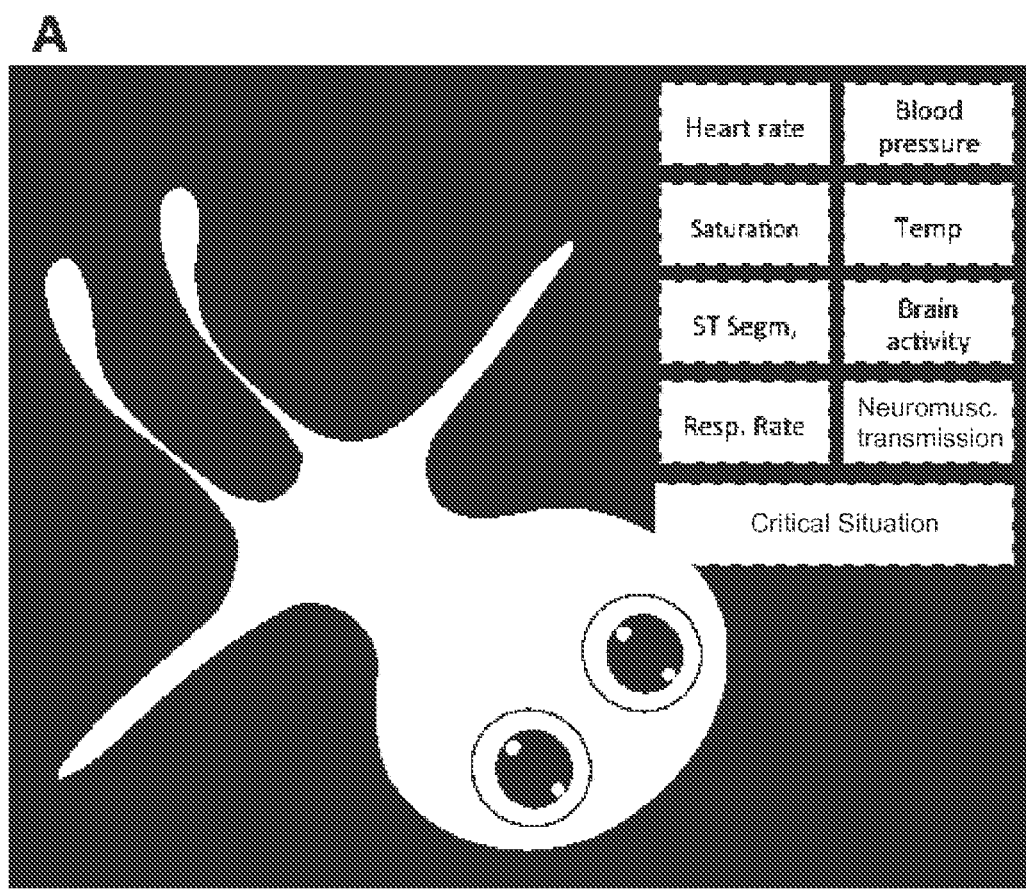
FIG. 45A

METHOD AND SYSTEM FOR MONITORING A PATIENT'S MEDICAL CONDITION

CROSS-REFERENCE TO RELATED APPLICATIONS

This application claims priority to, and is a continuation of, International Application No. PCT/EP2016/060931, filed May 14, 2016, claiming priority to European Patent Application No. EP20150168778, filed May 21, 2015, both of which priority applications are hereby, incorporated by reference herein in their entireties.

TECHNICAL FIELD

This disclosure relates to a method, a computer program and a system for monitoring and visualizing a patient's medical condition.

BACKGROUND

Contemporary health care settings such as intensive care units, intermediate care units, operating rooms, hospital wards, ambulances and medevac helicopters make extensive use of devices showing patient monitoring data increasingly featuring powerful computers and large format flat screen displays. Furthermore, monitoring data is being used and displayed in telemedicine products, online and offline hardware and software applications, and a wide scope of consumer health products (e.g., e-health applications for smart devices), for use at home or in retirement homes.

Modern day monitoring devices display a multitude of monitoring parameters, e.g., ECG, blood pressure, oxygen saturation, respiratory rate, and expiratory CO2. These parameters are displayed either as natural numbers or graphically as a waveform. E.g., current monitors may show blood pressure values numerically from 0-300 mm Hg or as a waveform, showing the value of a parameter over time, but not as an intuitively understandable single display (or instrument).

A contemporary patient monitor may display twenty or more different raw data points and waveforms on a single screen.

However, the number of data points displayed is extremely large and simply overwhelms users with information. Depending on the number of parameters monitored, it becomes impossible to consistently comprehend all of the constantly changing information and remain aware of the patients' situation (situation awareness of the healthcare provider).

SUMMARY

A method for monitoring and visualizing a patient's medical condition includes displaying a graphical representation of the (e.g. human) patient (being particularly formed as a homunculus) on a display device, The displayed graphical representation includes a body having at least a torso and a head (as well as two legs and two arms extending from the torso, respectively), wherein said displayed graphical representation includes at least one region which is allocated to at least one provided (e.g. measured or determined) patient monitoring quantity (e.g. provided in form of a data stream), and wherein said graphical representation or said at least one region is automatically rendered such that the appearance of the at least one region depends on, particularly corresponds to, the current value of the at least one patient monitoring quantity and/or such that the appearance of the at least one region is altered, preferably in real-time, when the at least one patient monitoring quantity, e.g. its current value, to which said at least one region is allocated, changes. The term "real-time" as used throughout this document is understood by a person skilled in the art of digital data processing as "near real-time" or "quasi real-time". Any digital data processing step (e.g., an image processing step) applied to data captured from the real world (e.g., sensor data to be transferred into visual representations of such sensor data) can result in a delay imposed by the digital data processing steps. For example, there is a rendering delay between the (sensed) event of a physical state change occurring in the clinical state of a patient and the corresponding (display) event of the respective visualization on a physical display. For convenience, only the term "real-time" will be used throughout this document when referring to such "near real-time" behavior of the disclosed methods and systems.

The present disclosure provides a method and system for rendering images (that can be displayed by a two- or three-dimensional (graphic) display device) of a synthetic patient model. The system may be provided either as an addition to a monitoring device (i.e., as a standalone device), may be incorporated/integrated into a conventional patient monitoring device, or may be configured to display said rendered images as a hologram.

The graphical representation of the patient or the homunculus is altered according to (e.g. raw) monitoring data inputs, that may be contained in a data stream or several separate data streams and are herein denoted as patient monitoring quantities. These quantities can be, but are not limited to: pulse rate (PR), peripheral oxygen saturation (OS), blood pressure (BP), body temperature (Temp), ECG QRS heart rate (HR), ECG rhythm detection (ECG), ECG ST-segment deflection (ST), right ventricular pressure (RVP), pulmonary capillary wedge pressure (PCWP), mixed venous oxygen saturation (MVOS), cardiac output (CO)/cardiac index (CI), central venous pressure (CVP), respiratory rate (RR), tidal volume (TV), expiratory carbon dioxide (eCO2), expiratory oxygen (eO2), brain activity (BIS, EEG), Intracranial pressure (ICP), brain tissue oxygenation tension (BO), neuromuscular transmission (NMT). Particularly, to render the image, the raw data is organized and processed according to algorithms and sent to a graphics processor for rendering. The respective patient monitoring quantity or quantities can either be measured using an appropriate sensor interacting with the patient or may be (e.g. automatically) derived from one or several measured quantities.

The present disclosure provides an instrument showing a synthetic rendering of the monitored patient according to the (e.g. raw) data input (e.g. patient monitoring quantities) representing the state of the actual patient.

In one aspect, the disclosed method uses alterations of the attributes of specified parts called regions of the graphical representation of the patient or of said homunculus, including their presence or absence, volume or area of regions (3D) or area (2D), and color.

Particularly, according to the algorithms incorporated into the system or used in conjunction with the disclosed method, the inputs of the individual (e.g. raw) patent monitoring data for each quantity/parameter cause alterations of the attributes of one or more regions of the graphical representation of the patient (e.g. homunculus).

Particularly, the disclosed method also proportions the extent of change of the regions of the graphical representation of the patient (e.g. homunculus) according to the data input (e.g. the patient monitoring quantities) and the algorithms. The required changes of the attributes of the regions of the visual patient representation (e.g. homunculus) are forwarded to a graphics processor for rendering as a two- or three-dimensional image that is displayed with said display device.

Particularly, in other words, the disclosure provides a computer generated instrument (e.g. comprising a graphical display), that synthesizes the (e.g. raw) monitoring data (e.g. the patient monitoring quantities) into a single dynamic two- or three-dimensional synthetic patient model that is displayed, particularly in real-time, representing the condition of the actual monitored patient according to the (e.g. raw) data input.

Compared to a conventional patient monitoring device, the disclosed system and method are easier for healthcare providers and personal consumers (e.g., users of e-health applications on smart devices) to interpret and to understand; an important advantage when they must make quick decisions.

Further, according to an embodiment of the disclosed method, some parameters (e.g., pulse rate, blood pressure, central venous pressure, respiratory frequency, tidal volume, expiratory $CO_2$, body temperature, etc.) have negative and positive abnormal ranges. For such parameters, the medical state may be represented by three simplified state values (e.g., "too low", "normal", and "too high"). Some parameters (e.g., oxygen saturation, brain activity, ST-segment, neuromuscular relaxation etc.) only have a negative abnormal and a normal range in which case the medical state may be represented by two simplified state values (e.g., "abnormal"/"too low" and "normal". Further simplified states may be defined. For example, there may be "critical" simplified state values which follow on a "too high" or "too low" state. By reducing the continuum of parameter/quantity values to the simplified discrete state value ranges (e.g., 2-state values, 3-state values, 4-state values, etc.) the amount of data to be rendered is reduced and, as a consequence, the complexity of rendering visual representations of such state values is reduced.

As disclosed in detail further down in this document, the rendered volume of the body of the patient's graphical representation may be changed between a first value derived from the current diastolic blood pressure (DBP) and a second value derived from the current systolic blood pressure (SBP). The re-rendering of the volume may be performed in particular with a frequency associated to the pulse rate (PR). Thereby, the pulse rate of a patient is rated as "normal" in an interval comprising a lower threshold value and a higher threshold value. If the pulse rate falls below the lower threshold value, the associated simplified state value switches from "normal" to "too low". If the pulse rate raises beyond the higher threshold value, the associated simplified state value switches from "normal" to "too high". If the pulse rate raises beyond a critical threshold value, the associated simplified state value may switch from "too high" to "critical". That is, a particular range or interval (as defined by the respective threshold values) of monitored pulse frequencies is associated with a corresponding simplified state value. In general, for each parameter where the graphical representation indicates a medical state of the patient through periodic re-rendering at a frequency which is associated with a frequency of the monitored parameter, one or more threshold values can be defined as state switching threshold values. When the monitored parameter exceeds such a state switching threshold value in either direction, a corresponding state change is detected with regards to the simplified states associated with the monitored parameter. This may be applied to multiple monitored parameters in parallel.

The re-rendering of the respective graphical representation(s) can now occur at pre-defined rendering frequencies which are associated with the simplified state values of the corresponding monitored parameters. That is, instead of re-rendering the graphical representation with a continuous frequency range that corresponds to the actually monitored parameter quantities, the system uses only a low number of frequencies (e.g., three frequencies for the simplified three state value scenarios, or two frequencies for the two state value scenarios). In general, re-rendering of the parts of the graphical representation affected by the monitored parameter occurs at a first re-rendering frequency associated with a first simplified state when the current value of the at least one patient monitoring quantity falls into a first range of patient monitoring quantities associated with the first simplified state, and occurs at a second re-rendering frequency associated with a second simplified state when the current value of the at least one patient monitoring quantity falls into a second range of patient monitoring quantities associated with the second simplified state. As a consequence, changes of the rendering frequency occur only in cases where the corresponding monitored parameter quantity crosses a pre-defined threshold value indicating a simplified state change. For a human observer, a switch between the frequencies associated with the simplified states (e.g., from 60 Hz to 30 Hz) can easily be recognized whereas a continuous change (e.g., 60 Hz→59 Hz→58 Hz→etc.) is hardly recognizable by the human observer.

The rendering frequency values associated with the various simplified state representations may be defined to achieve high inter-rater agreement for a significant sample of different users. That is, a significant sample group of users rate the rendering frequencies in that each frequency is associated with a simplified state by each user for a particular monitored parameter. For example, by determining a median for each simplified state such frequencies can be identified which provide a high inter-rater reliability with regards to the visual representation of the respective simplified state for a majority of the users.

Particularly, the present disclosure provides the visual patient monitoring instrument from data received from patient monitoring devices (respectively the sensors applied to the patient, e.g. SpO2 sensor) and software, from data stored in a relational database, or from other methods that come to mind to those skilled in the art.

Particularly, according to an embodiment, a plurality of patient monitoring quantities is provided (e.g. measured and/or determined), wherein said displayed graphical representation (e.g. homunculus) comprises a plurality of regions, wherein each region is allocated to at least one of said patient monitoring signals, and wherein the appearance of the respective region depends on the current value of the at least one associated patient monitoring signal to which the respective region is allocated and/or wherein the appearance of the respective region is altered, particularly in real-time, when the at least one measured patient monitoring signal to which the respective region is allocated changes.

According to an embodiment of the disclosed method, the graphical representation of the patient is displayed such that it creates the impression of being looked at from the top, as is the usual anesthesiologists point of view when standing at the anesthesiologists position at the head of a patient, wherein particularly the point of view is a 45° angle from the head with a 30° angle of tilt upwards. However deviations from these angles are possible, too.

In other words, with respect to said fictitious beholder (e.g. physician) standing upright in front of the graphical representation/homunculus, said angle from the head means the angle that is enclosed by a projection of the viewing direction on the horizontal or coronal plane of the graphical representation/homunculus and the longitudinal axis of the graphical representation/homunculus. Further, the angle characterizing said tilt is the angle enclosed by the horizontal or coronal plane of the graphical representation/homunculus and the viewing direction (see e.g., o FIGS. 2A, 2B and 2C).

Further, according to an embodiment of the disclosed method, the graphical representation of the patient is adapted to characteristics of the patient, particularly to its gender, age, weight, height, medical conditions. (e.g. obesity).

Further, according to an embodiment of the disclosed method, bars may be shown above or below alarm fields to indicate the magnitude of deviation from a normal value of a patient monitoring quantity (also denoted as patient monitoring data point). The length and the color of the bar may indicate the magnitude of deviation from the normal value. The position of the bar on the upper or lower border of the alarm field may indicate a deviation above (upper border) or below (lower border) the normal range of the quantity in question.

Further, according to an embodiment of the disclosed method, alerts based on the recognition of critical situations may be generated and particularly displayed using said display device. Particularly, a critical situation alert is triggered when specific combinations of parameters or quantities (data points), as outlined e.g. below in Table 2, are detected to deviate above or below their pre-specified normal ranges.

Further, according to an embodiment of the disclosed method, the at least one patient monitoring quantity is one of:
  a blood pressure (BP), as systolic (SBP), and diastolic (DBP) pressure, or mean pressure (MAP), derived from SBP and DBP,
  a pulse rate (PR),
  an oxygen saturation (OS),
  a body temperature (BT),
  an ECG QRS heart rate (HR),
  an ECG rhythm detection (ECG),
  an ECG ST-segment deflection (ST),
  a right ventricular pressure (RPV),
  a pulmonary capillary wedge pressure (PCWP)
  a mixed venous oxygen saturation (MVOS)
  a cardiac output (CO) and cardiac index (CI)
  a central venous pressure (CVP),
  a respiratory rate (RR),
  a tidal volume (TV),
  an expiratory CO2 value (eCO2),
  a brain activity (BI, EEG),
  an intracranial pressure (ICP),
  a brain tissue oxygen tension (BO), and
  a neuromuscular transmission (NMT).

Of course, in case several such quantities are provided, these patient monitoring quantities can be an arbitrary selection of the above stated quantities.

Further, according to an embodiment of the disclosed method, said at least one region (comprising a volume, e.g. when displayed in 3D, or an area, e.g. when displayed in 2D) is one of the following regions:
  said body,
  a heart,
  a vena cava,
  an arterial system,
  a lung,
  an expiratory $CO_2$ cloud,
  an inspiratory oxygen cloud,
  an eye, and
  a hand.

Of course the homunculus can be divided or may comprise several regions, wherein each region can be one of the regions described above. Further, each of these regions may be allocated to one or several of the above-stated quantities (data points). Thus, the disclosed method can display the medical condition of the respective patient in an intuitive manner that can be much more rapidly assessed by a physician or monitoring person than a mere display of data points whose relations to certain anatomic and physiologic features of the patient/homunculus is not shown.

Further, according to an embodiment of the method according to the present disclosure the displayed volume of the body of the graphical representation changes between a first value derived from the current diastolic blood pressure (DBP) and a second value derived from the current systolic blood pressure (SBP), particularly with a frequency associated to the pulse rate (PR). Here, preferably, the first value is smaller than the second value.

Further, according to an embodiment of the method according to the present disclosure a colour of the body of the graphical representation is altered when said oxygen saturation (OS) changes.

Further, according to an embodiment of the disclosed method, the appearance of said graphical representation (e.g. homunculus) or body is altered when the current body temperature changes, wherein particularly a change of the body temperature leads to a change in an amount and/or the appearance of temperature indicators displayed on or adjacent to said body, wherein particularly said temperature indicators for temperatures lower than a pre-defined normal temperature range (e.g. 36° to 37° C.) are formed as icicles and/or snowflakes, and wherein temperature indicators for temperatures higher than said pre-defined normal temperature are manifested in one or more of the following or similar visualizations on the graphical display: sweat pearls, heat waves, and flames.

Further, according to an embodiment of the disclosed method, the displayed volume of the heart is altered between a first value derived from the current diastolic blood pressure (DBP) and a second value derived from the current systolic blood pressure (SBP), particularly with a frequency associated to the ECG QRS heart rate (HR). Here, particularly, the first value is smaller than the second value.

Further, according to an embodiment of the disclosed method, the displayed volume of the vena cava is associated to the value of the current mean central venous pressure (CVP), wherein the displayed volume of the vena cava is altered when the current mean central venous pressure (CVP) changes, wherein particularly the displayed volume of the vena cava is proportional to the current mean central venous pressure (CVP).

Further, according to an embodiment of the disclosed method, the displayed volume of the lung is altered between a first value and a second value derived from the tidal volume (TV), respectively, particularly with a frequency associated to the respiratory rate (RR), wherein particularly the first value is smaller than the second value.

Further, according to an embodiment of the disclosed method, the displayed volume of the expiratory $CO_2$ cloud is altered between a first value and a second value derived from the capnographic value (CAP), respectively, particularly with a frequency associated to the respiratory rate (RR), wherein particularly the first value is smaller than the second value.

Further, according to an embodiment of the disclosed method, the appearance of the eye is altered when the bispectral index (BI) or electroencephalogram (EEG) value changes (e.g. by a pre-defined threshold amount), wherein particularly a first range of the bispectral index (BI) or electroencephalogram (EEG) value is associated to a display of the eye in an open state and a second range of the bispectral index (BI) or electroencephalogram (EEG) value is associated to a display of the eye in a closed state, wherein particularly a third, in-between range of the bispectral index (BI) or electroencephalogram (EEG) value is associated to a display of the eye in a partially open state.

Further, according to an embodiment of the disclosed method, the appearance of the hand is altered when the neuromuscular transmission (NMT) value changes (e.g. by a pre-defined threshold amount), wherein particularly a first range of the neuromuscular transmission (NMT) value is associated to a display of relaxed hands and a second range of the neuromuscular transmission (NMT) value is associated to the display of an extended thumb and a closed first of said hand (i.e., representing a thumbs up gesture).

Further, according to an embodiment of the disclosed method, the change in volume and/or appearance of the at least one region of said graphical representation (or of some or all of the used regions) is displayed using a smoothing function, so as to provide smoother changes in volume and/or appearance at the lower and the higher ends of the range of the input parameters (e.g. patient monitoring quantities). This is applied to enable the user to detect lower and higher extreme values more easily. A mathematical description of an example of such a function is: a smooth, monotonically increasing function, which is convex for a first part of a range of an input parameter (e.g. patient monitoring quantity) and concave for a succeeding second part of said range. As an example, a specific form of this function f(x) can be described as follows:

$$f(x)=(\sin(\pi*x/x_{max}-\pi/2)+1)*y_{max}/2,$$

where x is the input parameter (e.g. patient monitoring quantity) within the interval [0; $x_{max}$] and $y_{max}$ the maximum result (i.e., the maximum change in volume and/or appearance of the at least one region of said graphical representation). For example, in case the values for the blood pressure (BP) range from 0-250, the values from 0 to 125 lie on the first convex part of the smoothing function (graph is curved to the left), whereas the values from 125 to 250 lie on the second concave part of the smoothing function (graph is curved to the right).

According to a further aspect of the present disclosure, a computer program is provided. This computer program for monitoring and visualizing a patient's medical condition, comprises program code that is adapted to conduct the method, according to the disclosure, as described herein when the computer program is executed on a computer.

Particularly, the at least one patient monitoring quantity or one or several of these quantities described herein are provided as an input used by the computer program.

Particularly, the features of the method, according to the disclosure, may also be used to further specify the computer program according to the disclosure, wherein the respective patient monitoring quantities that are measured or provided in the context of the method, according to the disclosure, are provided as an input used by the computer program.

According to yet another aspect of the present disclosure, relates to a system for monitoring and visualizing a patient's medical condition, wherein the system comprises a display device and is configured to conduct the method, as described herein (see e.g., above).

For this, particularly, the system may comprise a processing device connected to the display device that is adapted to conduct the method using the display device. The processing device can comprise a computer on which a computer program, according to the disclosure, is executed. Other configurations are also possible (see e.g., above).

In the following, further aspects, and embodiments of these aspects, are referred to as numbered points 1-20 (the reference numerals relate to the Figures). Points 1-20 are:

1. A method for monitoring and visualizing a patient's medical condition, wherein a graphical representation (10) of the patient (P) comprising a body (1) having at least a torso (1a) and a head (1b) is displayed using a display device (20), wherein at least one patient monitoring quantity is provided, and wherein said displayed graphical representation (10) comprises at least one region (1, 1a, 1b, 1c, 1d, 2, 3, 4, 5, 6, 7, 8, 9) which is allocated to said at least one patient monitoring quantity, and wherein the appearance of the at least one region depends on the current value of the at least one patient monitoring quantity and/or wherein the appearance of the at least one region is altered, particularly in real-time, when the current value of the at least one patient monitoring quantity to which said at least one region is allocated changes.

2. The method according to point 1, wherein the graphical representation (10) further comprises two arms (1c) and/or two legs (1d) which extend from the torso (1a), respectively.

3. The method according to point 1 or 2, wherein a plurality of patient monitoring quantities is provided, wherein said displayed graphical representation (10) comprises a plurality of regions (1, 1a, 1b, 1c, 1d, 2, 3, 4, 5, 6, 7, 8, 9), wherein each region is allocated to at least one patient monitoring quantity of said plurality of patient monitoring quantities, and wherein the appearance of the respective region depends on the current value of the at least one patient monitoring quantity to which the respective region is allocated and/or wherein the appearance of the respective region is altered, particularly in real-time, when the current value of the at least one patient monitoring quantity to which the respective region is allocated changes.

4. The method according to one of the preceding points, wherein the graphical representation (10) of the patient (P) is displayed such that it creates the impression of being looked at from the top, wherein particularly the point of view is a 45° angle (A) from the head with a 30° angle (A') of tilt upwards.

5. The method according to one of the preceding point, wherein the graphical representation (10) of the patient (P) is adapted to characteristics of the patient (P), particularly to its gender, age, weight, height, and/or one or several medical conditions.

6. The method according to one of the preceding points, wherein the at least one patient monitoring quantity represents one of the following quantities or that the plurality of patient monitoring quantities is selected from the following quantities:

a blood pressure (BP), as systolic (SBP), and diastolic (DBP) pressure, or mean pressure (MAP), derived from SBP and DBP.

a pulse rate (PR),
an oxygen saturation (OS),
a body temperature (BT),
an ECG QRS heart rate (HR),
an ECG rhythm detection (ECG)
an ECG ST-segment deflection (ST)
a right ventricular pressure (RPV)
a pulmonary capillary wedge pressure (PCWP)
a mixed venous oxygen saturation (MVOS)
a cardiac output (CO) and cardiac index (CI)
a central venous pressure (CVP),
a respiratory rate (RR),
a tidal volume (TV),
an expiratory CO2 value (eCO2),
a brain activity (BI, EEG),
an intracranial pressure (ICP),
a brain tissue oxygen tension (BO), and
a neuromuscular transmission (NMT).

7. The method according to one of the preceding points, wherein said at least one region is one of the following regions, or that said plurality of regions is selected from the following regions:
said body (1),
a heart (2),
an arterial system (3)
a vena cava (4),
a lung (5),
an expiratory $CO_2$ cloud (6),
an eye (7),
a brain (8) and
a hand (9).

8. The method according to points 6 and 7, wherein the displayed volume of the body (1) of the graphical representation (10) is changed between a first value derived from the current diastolic blood pressure (DBP) and a second value derived from the current systolic blood pressure (SBP), particularly with a frequency associated to the pulse rate (PR), wherein particularly said first value is smaller than the second value.

9. The method according to one of the points 6 to 8, wherein color of the body (1) or of a part of the body (1) of the graphical representation (10) is altered when said oxygen saturation (OS) changes.

10. The method according to one of the points 6 to 9, wherein the appearance of said graphical representation (10) or body (1) is altered when the body temperature changes, wherein particularly an amount and/or the appearance of temperature indicators (11) displayed on or adjacent to said body is altered when the current body temperature (BT) changes, wherein particularly said displayed temperature indicators (11) for temperatures lower than a pre-defined normal temperature are formed as icicles and/or snowflakes, and wherein particularly temperature indicators (11) for temperatures higher than said pre-defined normal temperature are formed as sweat pearls and/or heat waves rising from the body (1).

11. The method according to one of the point 6 to 10, wherein the displayed volume of the heart (2) is changed between a first value derived from the current diastolic blood pressure (DBP) and a second value derived from the current systolic blood pressure (SBP), particularly with a frequency associated to the ECG QRS heart rate (HR), wherein particularly the first value is smaller than the second value.

12. The method according to one of the points 6 to 11, wherein the appearance of the heart (2) is altered according to the current ECG rhythm, which ECG rhythm is particularly detected by an ECG rhythm detection system (ECG), and wherein particularly when a specific heart rhythm is detected an associated electrical conduction path or an electrical heart activity (14) is displayed on the heart (2) using the display device (20).

13. The method according to one of the points 6 to 12, wherein the displayed volume of the vena cava (4) is associated to the current value of the mean central venous pressure (CVP), wherein the displayed volume of the vena cava (4) is altered when the current value of the mean central venous pressure (CVP) changes, wherein particularly the displayed volume of the vena cava (4) is proportional to the current value of the mean central venous pressure (CVP).

14. The method according to one of the points 6 to 13, wherein the displayed volume of the lung (5) is altered between a first value and a second value derived from the tidal volume (TV), respectively, particularly with a frequency associated to the respiratory rate (RR), wherein particularly the first value is smaller than the second value.

15. The method according to one of the points 6 to 14, wherein the displayed volume of the expiratory $CO_2$ cloud (6) is altered between a first value and a second value derived from the capnographic value (CAP), respectively, particularly with a frequency associated to the respiratory rate (RR), wherein particularly the first value is smaller than the second value.

16. The method according to one of the points 6 to 15, wherein the appearance of the eye (7) is altered when the bispectral index (BI) value changes, wherein particularly when said index (BI) lies in a first range the eye (7) is displayed in an open state (7a), and wherein particularly when said index (BI) lies in a second range the eye (7) is displayed in a closed state (7b), and wherein particularly when said index (BI) is in a third range the eye (7) is displayed in a partially open state (7c).

17. The method according to one of the points 6 to 16, wherein the appearance of the hand (9) is altered when the current neuromuscular transmission (NMT) value changes, wherein particularly when said neuromuscular transmission (NMT) value lies in a first range the hand (9) is displayed in a first state, particularly in a relaxed state, and wherein particularly when said neuromuscular transmission (NMT) value lies in a second range the hand (9) is displayed in a different second state, particularly in a state with an extended thumb and tightened fingers.

18. The method according to one of the preceding points, wherein the change in volume and/or appearance of the at least one region (1-9) of said graphical representation (10) is displayed using a smoothing function in the form of a monotonically increasing function, which is convex for a first interval of a range of an input parameter and concave for a succeeding different second interval of said range.

A further aspect relates to:

19. A computer program for monitoring and visualizing a patient's medical condition, wherein the computer program comprises program code that is adapted to conduct the method according to one of the points 1 to 18 when the computer program is executed on a computer.

Yet, a further aspect relates to:

20. A system for monitoring and visualizing a patient's medical condition, wherein the system comprises a display device (20) and is configured to conduct the method according to one of the points 1 to 18.

Further features and advantages of the disclosed systems and methods will become apparent to those of ordinary skill in the art in view of the detailed description which follows, when considered together with the attached drawings and claims.

BRIEF DESCRIPTION OF THE DRAWINGS

FIG. 44 is an illustration of graphical examples of the changes in the relative positions of the sections of part 1 of the homunculus, representing the arms, legs, and head according to neuromuscular transmission measurements.

FIGS. 45A, 45B and 45C are illustrations of graphical examples of how an alarm system representing an annunciator panel and including a critical situation alarm system may be implemented according to an embodiment of the disclosure.

DETAILED DESCRIPTION

A system and a method are disclosed herein. The system and method synthesize multiple streams of raw patient monitoring data into a single display device 20 (or instrument), showing a synthetic model of the monitored patient P, which is generated according to algorithms and rendered dynamically, particularly in real-time, by a graphics processor 21 (cf. FIG. 5). In contrast thereto, in traditional patient monitoring, the patient monitoring data are displayed as a multitude of individual numbers or waveforms, which are difficult to observe, particularly in stressful situations. Here, the disclosed system and method offer, among others, the advantageous technical effect of providing the medical information in the context of the actual body regions to which they are associated so that a fast and intuitive understanding of the complete medical condition of the patient P is supported.

Figure 1:
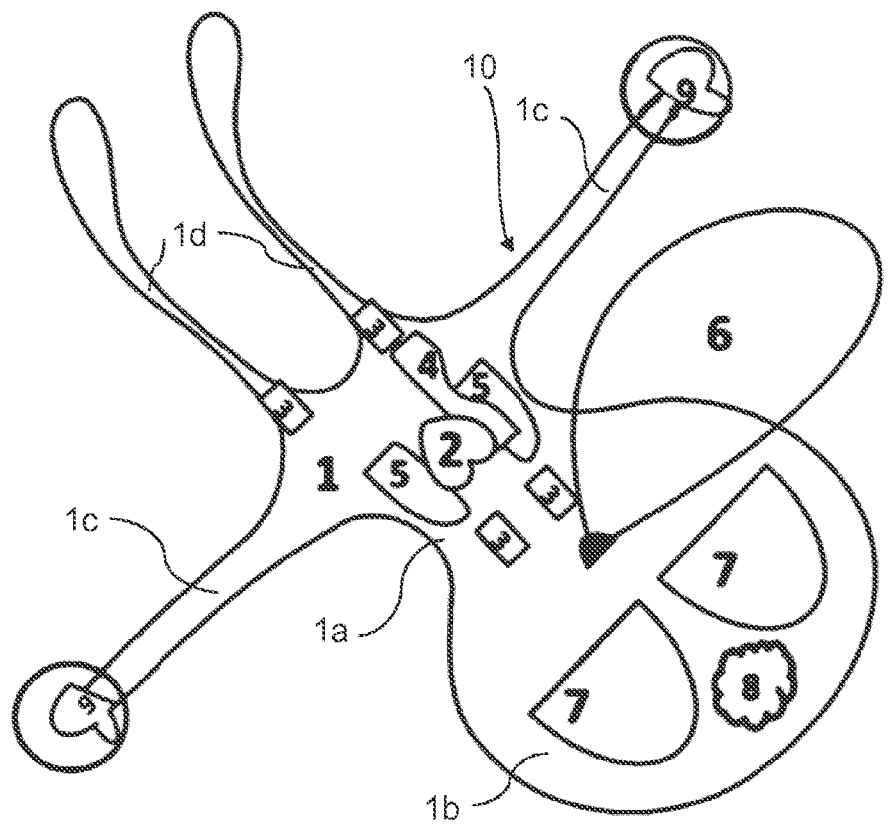
FIG. 1 is an illustration of the parts of the homunculus 1-9, which are rendered according to the disclosure.
Figure 2A:
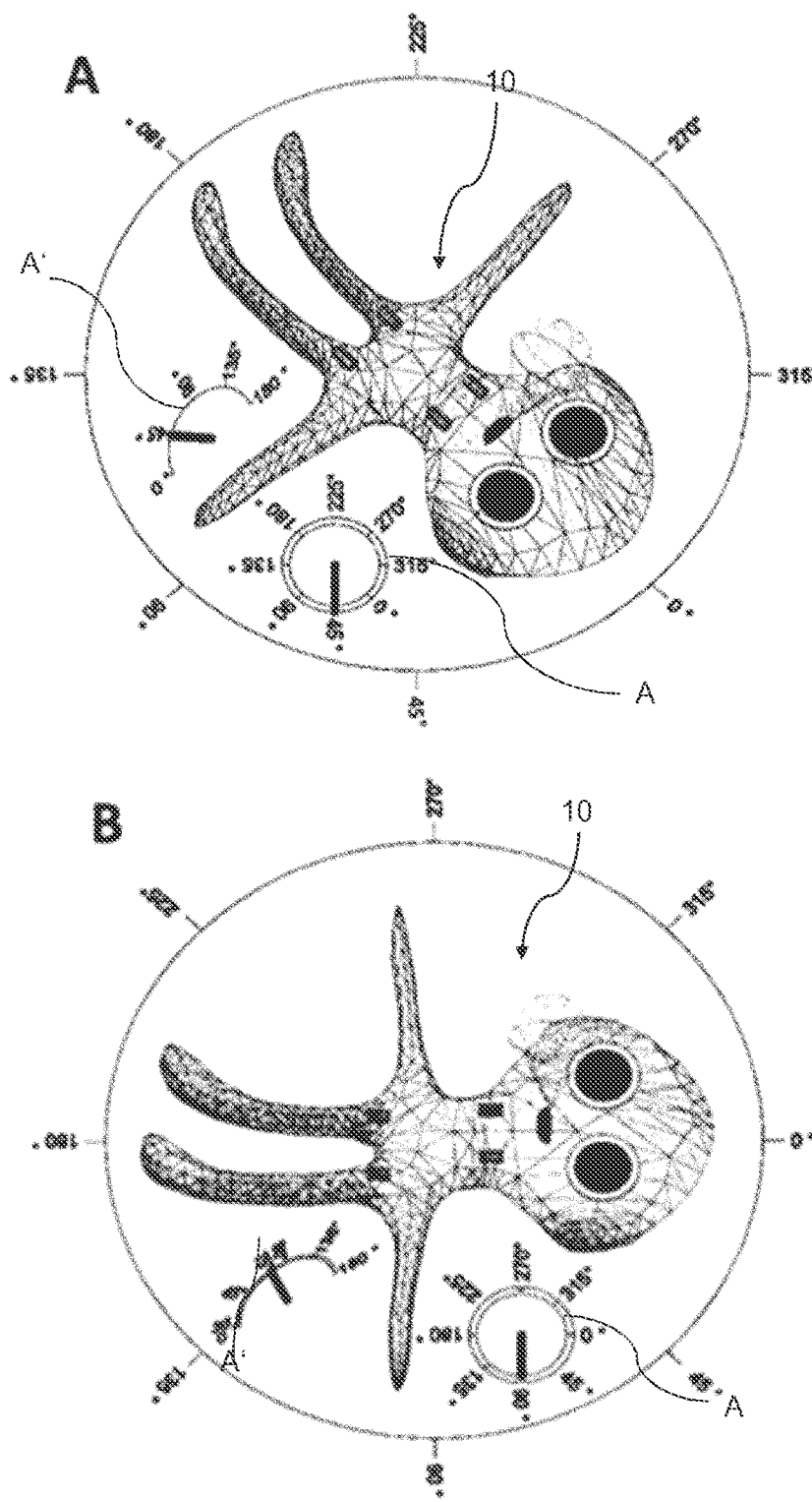
FIGS. 2A, 2B, and 2C are illustrations of various examples of angles of view of the homunculus.
Figure 2B:
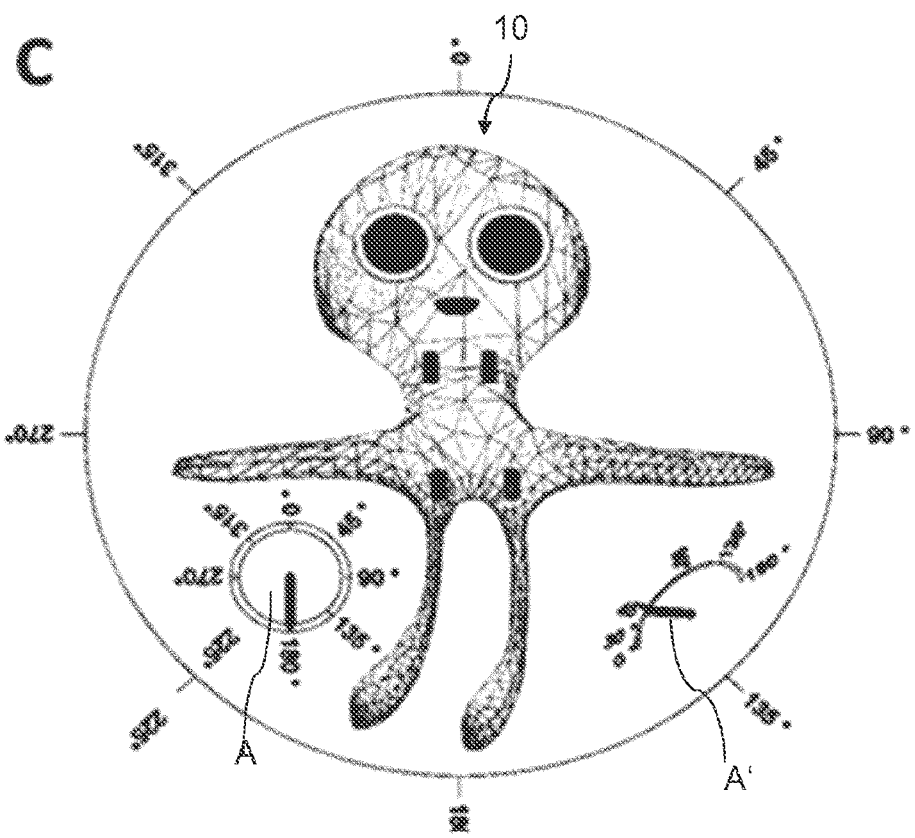
Figure 2B:
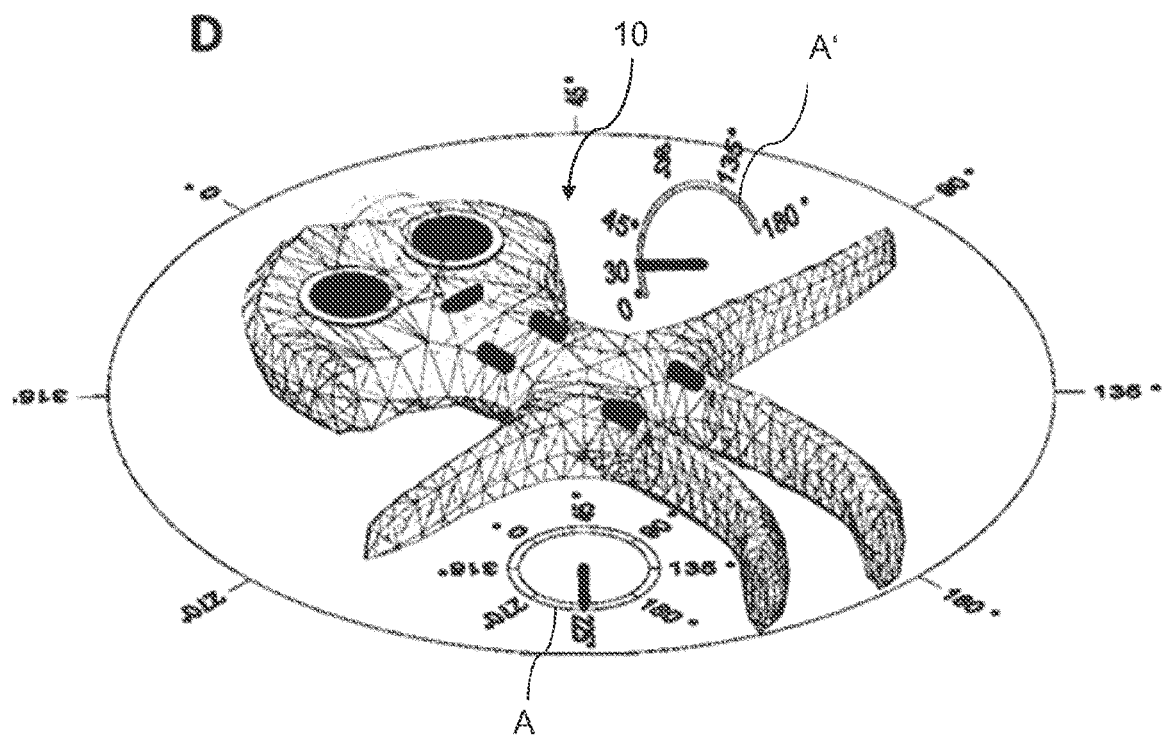
Figure 2C:
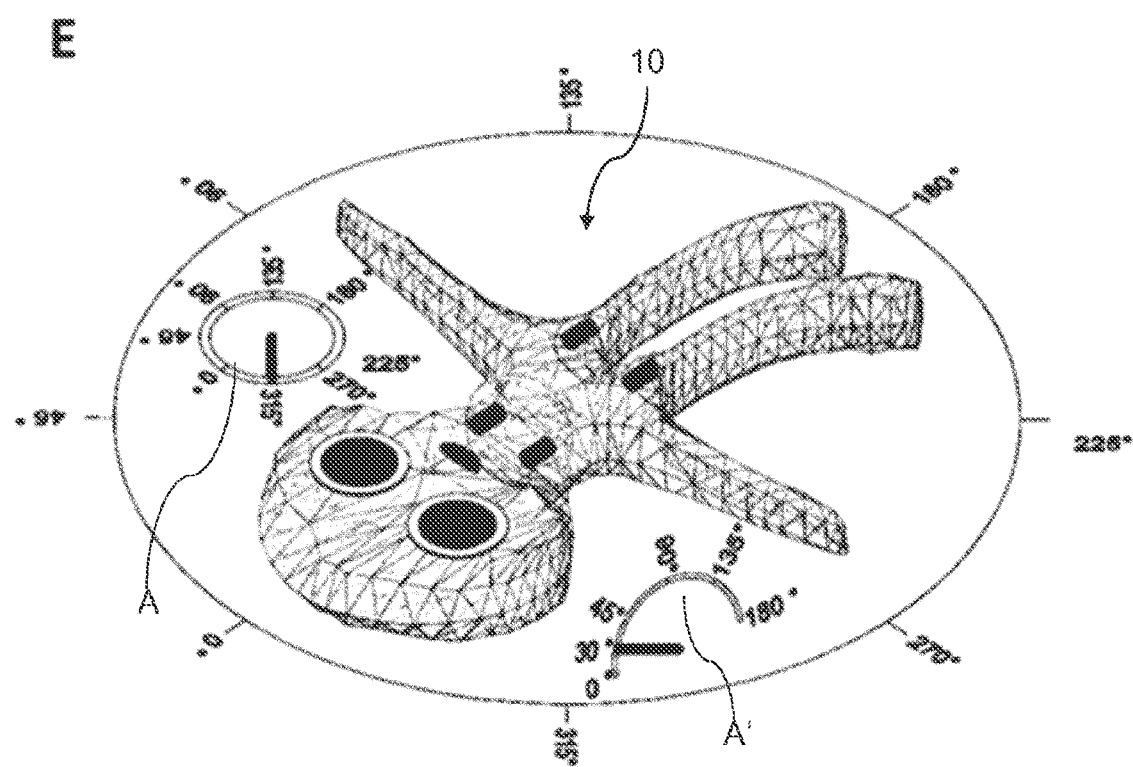

FIG. 1 shows a possible basic design of an automatically rendered graphical representation 10 of a patient P in the form of a homunculus 10, according to an embodiment, as well as the parts or regions 1 to 9 of the homunculus that are automatically altered by the disclosed system and method. Particularly, the homunculus comprises a body 1 that may be indicated by a circumferential outline, which body 1 comprises at least a torso 1a and a head 1b extending from the torso 1a, as well as preferably two arms 1c (particularly with hands 9 and particularly fingers, respectively) and two legs 1d extending from the torso 1a, respectively. Particularly, as shown e.g. in FIG. 1, said parts or regions can be: said body 1, a heart 2, an arterial system 3, a vena cava 4, a lung 5, an expiratory $CO_2$ cloud 6 that is exhaled by the head 1b of the homunculus 10, at least one eye 7 (preferably two eyes 7), a brain 8 and at least one hand 9, particularly two hands 9. Further body regions may also be used.

The dynamic alterations of the states of the parts or regions 1 to 9 of the homunculus 10 include their presence or absence, as well as changes in volume, area, length and color of parts/regions 1 to 9. The homunculus 10 may be looked at from all angles according to user input. An embodiment places the point of view at an angle A of 45 degrees from the head 1b of the homunculus 10 with an angle A' of 45 degrees of tilt. Various angles A, A' of view of the homunculus 10 are shown in FIG. 2.

Figure 3:
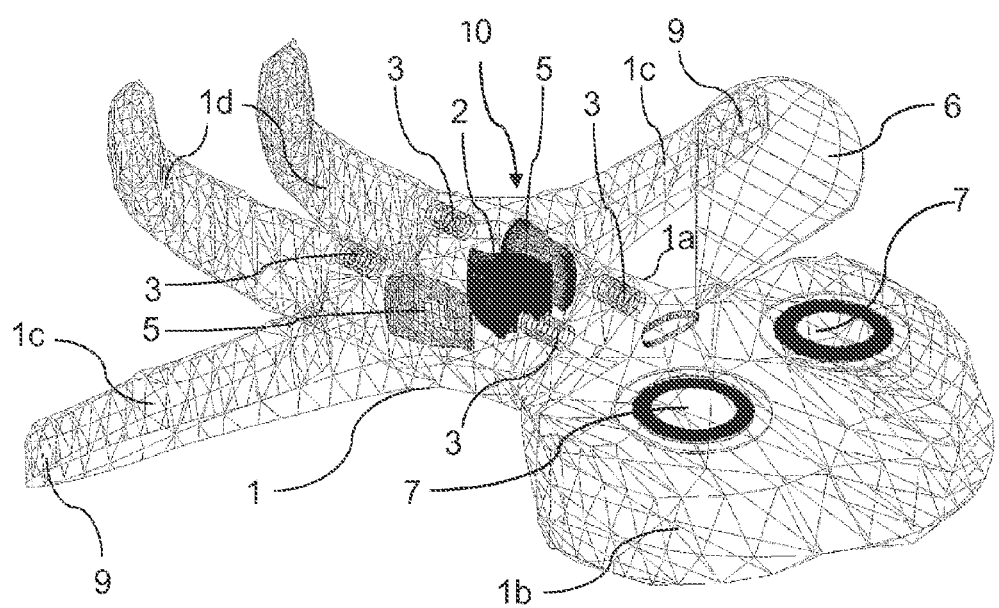
FIG. 3 is an illustration of a 3-dimensional embodiment of the visual patient display or instrument.

An embodiment of the disclosed method creates a dynamic rendering of a synthetic patient model, representing the condition of the actual monitored patient P according to the raw input data. The method uses alterations in the states (or attributes) of specified parts or regions 1 to 9 of a displayed homunculus 10, i.e., the representation of a human being (i.e., FIG. 1). The dynamic alterations include presence/absence of parts or regions, changes in volume and area of parts or regions (in a 3D embodiment), area of parts or regions (in a 2D embodiment) or even length of parts or regions and changes in color of parts or regions. An artistic impression of a 3D embodiment is shown in FIG. 3.

The present disclosure addresses the problem of presenting an appropriate synthesis of patient monitoring quantities to a health care provider or another user of a monitoring device (e.g., personal consumer using an e-health app). The disclosed system and method. present all monitoring information in a single, easy to understand instrument, which is dynamically rendered and shown on a display device 20 (i.e., FIGS. 4 A and B). It may be presented on a wearable electronics device such as smart glasses or augmented reality devices, or as a hologram (i.e., FIG. 4 C). The display of the instrument may be two or three-dimensional.

Figure 4:
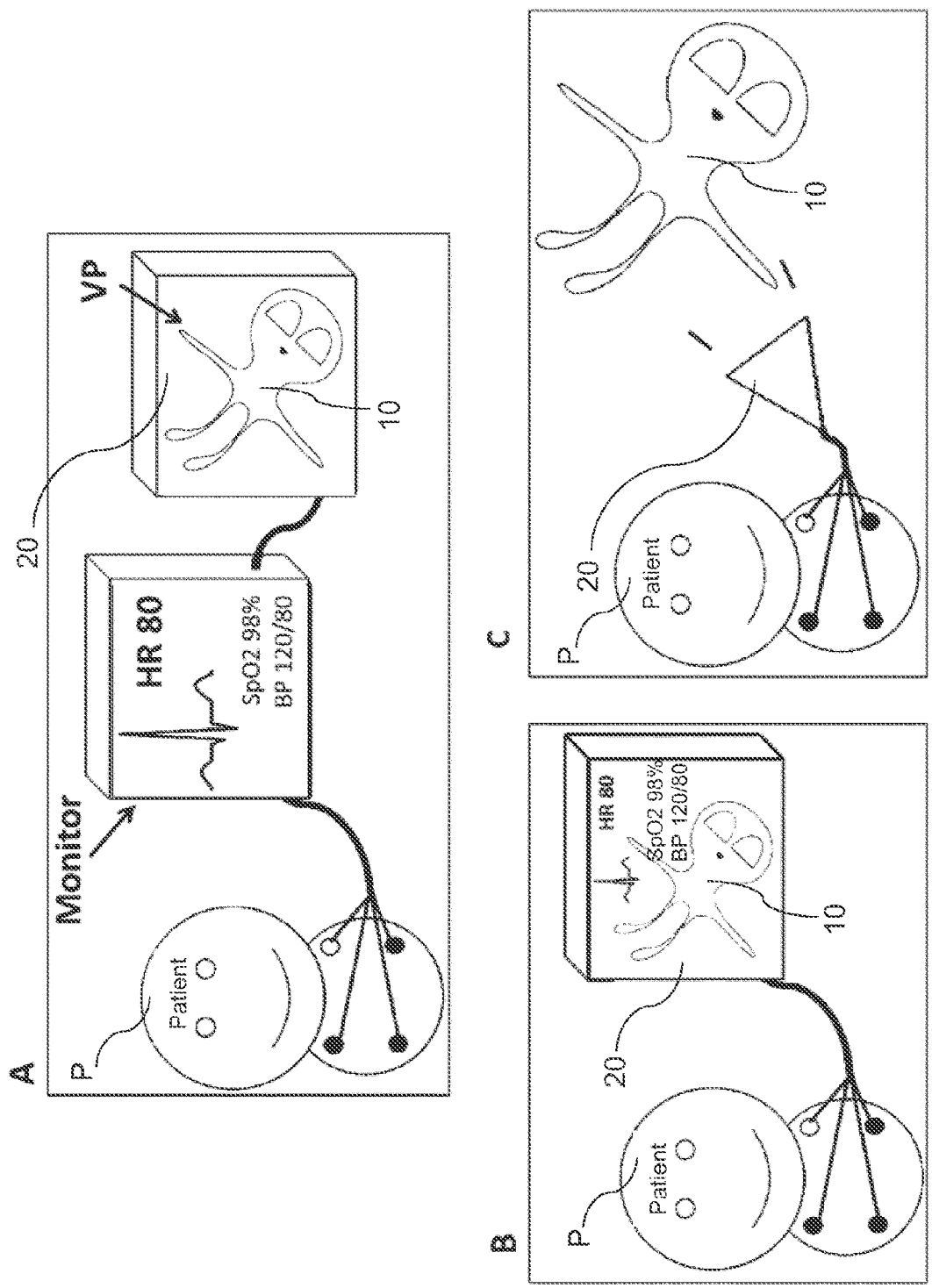
FIG. 4 is an illustration of various possible forms of applications of the disclosure.

According to FIG. 4, the visual patient display device 20 may be presented: A: as a separate standalone device in addition to a state-of-the-art patient monitoring device (Monitor), B: integrated with a conventional patient monitoring device (single monitor showing both the visual patient instrument and conventional monitoring data), or C: projected as a hologram.

The disclosed system and method are particularly suited to be used integrated with a conventional patient monitoring device (a single screen showing both the visual patient instrument and conventional monitoring data) and displayed together with the raw monitoring data, e.g. the image B shown in FIG. 4. However, it may also be used as a secondary separate instrument shown on a separate display, in addition to a primary patient monitoring device, i.e. the image A shown in FIG. 4. The display device 20 may be, for example, a cathode ray tube (CRT), a liquid crystal display (LCD) screen, a gas plasma-based flat-panel display, an organic light-emitting diode (OLED) display, an augmented reality (AR) device such as a head-mounted display (HMD), e.g. virtual reality headset, eyeglasses, contact lenses or any other form of AR device. Furthermore, the visualization may be presented on a computerized wristwatch (smart watch), as a hologram (e.g. as shown in FIG. 4 C), or other devices suitable for display of the instrument.

The present disclosure provides for the creation of a two- or three-dimensional instrument from the synthesis of raw monitoring data. According to the raw monitoring data, the disclosed system and method create a homunculus 10, which is a synthetic representation of the condition of the actual monitored patient. A graphics processor 21 dynamically renders the image.

Figure 5:
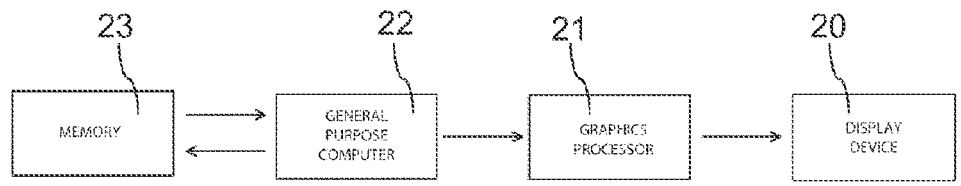
FIG. 5 is an illustration of a schematic overview of the system.

An overview of the system for carrying out the disclosed method is shown schematically in FIG. 5. The system includes a computer 22 (which may be a general purpose computer or a dedicated, specially designed computer), the memory 23 containing the software code with the algorithms, a graphics processor 21, and a display device 20.

Figure 6:
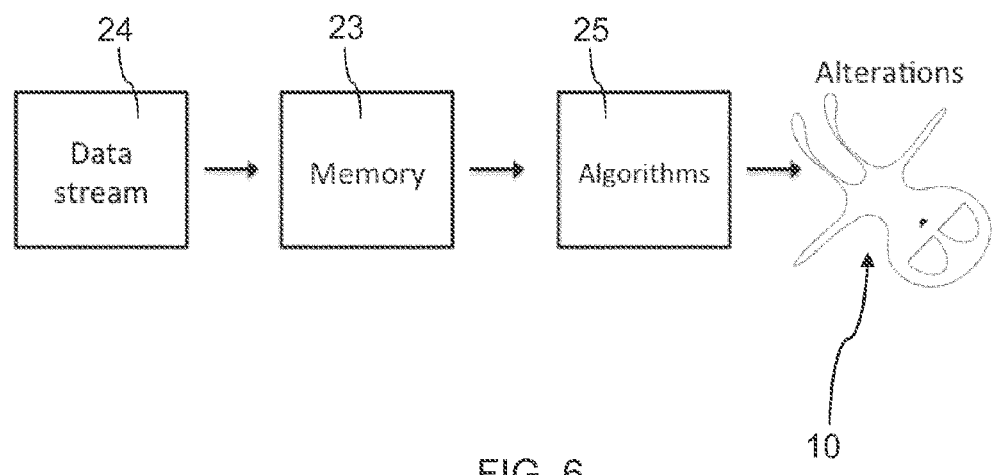
FIG. 6 is an illustration of a schematic overview of the process of creating an appropriate synthesis of patient monitoring parameters according to the disclosed visual patient monitoring algorithm.

The process of rendering an instrument from the raw patient monitoring data takes place in two broad steps, which are detailed hereafter and outlined in FIG. 6.

In step 1 the raw input data (i.e., "DATA STREAM" in FIG. 6) is loaded into system memory (i.e., "MEMORY" in FIG. 6) and is transformed by the general purpose computer into patient monitoring quantities (also denoted as data points), which can be utilized directly by the disclosed system and method. The raw monitoring data may come from commercially (or otherwise) available sensors (e.g., a pulse oximeter) and devices or software output, e.g. a simulator or a relational database. A data stream containing at least one, several or all of the following patient monitoring parameters or raw data: pulse rate (PR), oxygen saturation (SpO2), blood pressure (BP), body temperature (Temp), ECG QRS heart rate (HR), ECG rhythm detection (ECG), ST-segment deflection (ST), right ventricular pressure (RVP), pulmonary capillary wedge pressure (PCWP), mixed venous oxygen saturation (MVOS), cardiac output (CO)/ cardiac index (CI), central venous pressure (CVP), respiratory rate (RR), tidal volume (TV), expiratory carbon dioxide (eCO2), expiratory oxygen (eO2), brain activity (BIS, EEG), Intracranial pressure (ICP), brain tissue oxygenation tension (BO), neuromuscular transmission (NMT) is loaded into the memory 23 and is particularly transformed so that each patient monitoring quantity or data point can be utilized directly by the disclosed system and method. This generation of patient monitoring quantities or data points is continuously repeated as data is retrieved from the monitoring device. The resulting patient monitoring quantities or data points are a representation of each patient monitoring parameter (raw data). Data points originate from sensor data, e.g., pressures, volumes, and saturations, without regard to the initial format and within a certain range. If the raw patient data from the sensors is processed on-site, it is loaded directly into the memory 23. If it is delivered from a remote patient monitoring device, an additional data store is prepared as required. However, raw data may also be used without further processing as a patient monitoring quantity.

Figure 7:
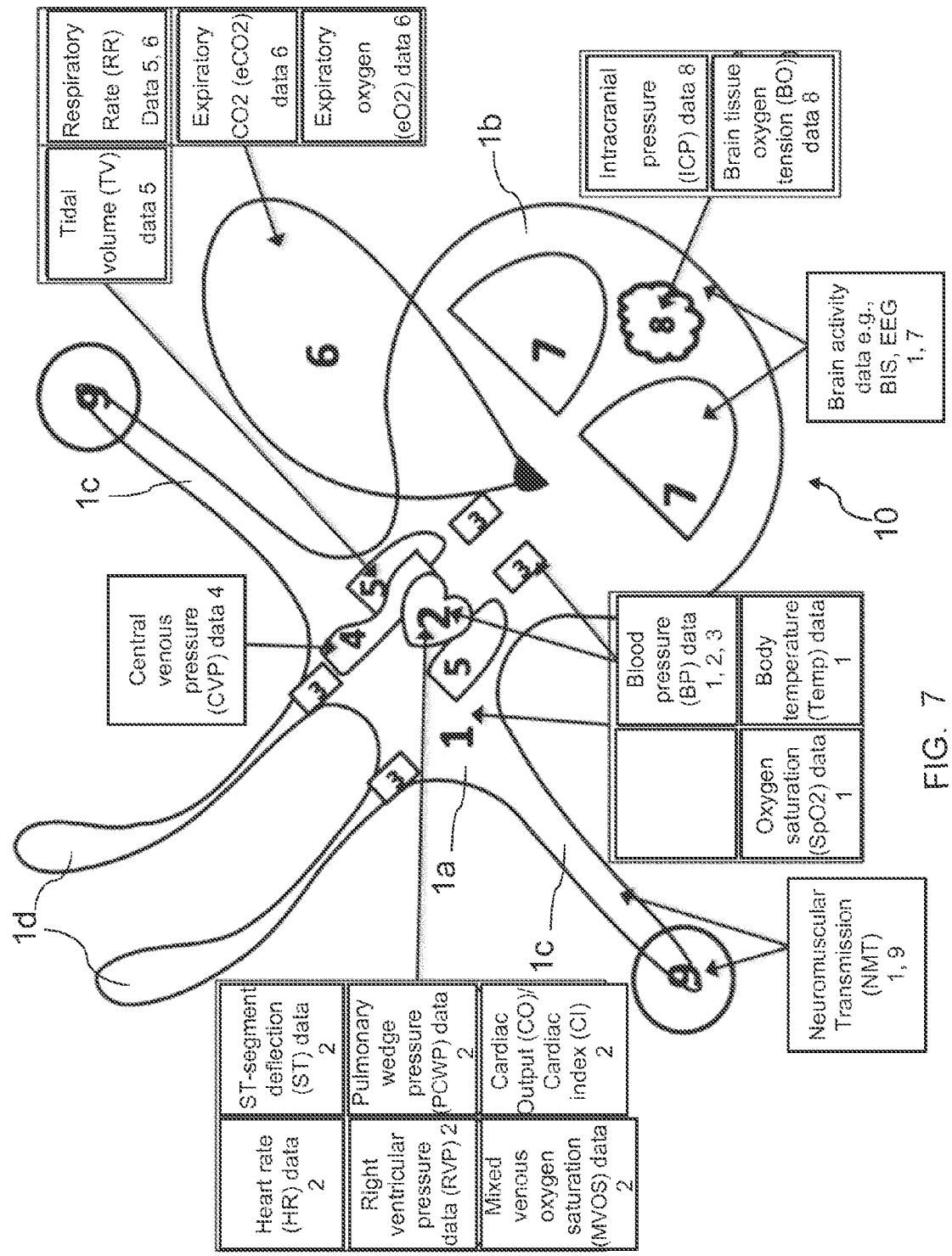
FIG. 7 is an illustration of a schematic overview of the allocation of the data streams to parts of the homunculus (parts 1-9).

In step 2, the patient monitoring quantities (data points) are transformed by the e.g. general purpose computer 22 according to the algorithms 25 of the present disclosure (e.g. FIG. 6) into one or multiple alterations in the states of specified parts or regions 1 to 9 of the homunculus 10. The method uses changes in the attributes of specified parts or regions 1 to 9 of the homunculus. These alterations (i.e., "ALTERATIONS" in FIG. 6) include the presence and absence of parts or regions 1 to 9, the volume or area of parts or regions 1 to 9 (3D) or area (2D) of parts or regions 1 to 9 or even length of parts or regions 1 to 9, and the color and movement of parts or regions 1 to 9 of the homunculus 10. The graphics processor 21 renders the image on a display device 20 (i.e., the parts or regions 1 to 9 of the homunculus 10 are changed dynamically) from the pertinent information. In order to establish data to render the image on the display device 20, data points are allocated to one or more representative parts or regions 1 to 9 of the homunculus 10 (cf. e.g. FIG. 7).

While one process of selecting one or more specific parts or regions 1 to 9 of the homunculus 10 for each data point has been disclosed, others are possible and other methods of assigning data points to parts or regions of the homunculus 10 will occur to those skilled in the art and may be used in applications without varying from the spirit of this disclosure.

According to an embodiment of the disclosure, the rendering of the e.g. real-time instrument, showing the synthetic model of the patient P takes place following the subroutines outlined hereafter (i.e., subroutines A and B).

While subroutine A (cf. FIG. 8) generates input data for subroutine B (cf. FIG. 9), they may be executed autonomously. In detail, subroutine A may generate data and temporarily store it in a data buffer until subroutine B consumes the data for further processing. Both subroutine A and subroutine B are connected through the overall visual patient monitoring algorithm (e.g. FIG. 6).

Subroutine A starts by computing an individual homunculus model 10 based on the monitored patients medical profile (i.e., age, weight, gender, height, pediatric, medical conditions, e.g. obesity) by altering a default homunculus model creating a "customized patient avatar". For example, if a patient is a woman, a homunculus having a body 1 representing a woman is displayed. The outcome (depicted as "INDIVIDUAL HOMUNCULUS MODEL" in FIG. 8) of this procedure (depicted as "COMPUTE INDIVIDUAL HOMUNCULUS MODEL" in FIG. 8) is used as an input for subroutine B (FIG. 9) of the algorithm.

After the individual homunculus model 10 has been established, the next step is to handle the incoming patient monitoring data. In case patient data arrives in form of a data stream ("RAW PATIENT MONITORING DATA STREAM" in FIG. 8), parameters that match the patient monitoring parameters monitored by the disclosed system and method, are extracted from the data stream, loaded into memory 23 and transformed into said data points (also denoted as patient monitoring quantities), as described in step one above. Then, these data points are associated with the current timestamp and added to the session data store ("ADD DATA POINTS TO SESSION DATA STORE" in FIG. 8) so that session trend information can be computed in a subsequent step ("COMPUTE SESSION TREND INFORMATION" in FIG. 8). Furthermore, session trend information is used as an input for subroutine B (FIG. 9) of the algorithm and may be represented on the display.

Next, the computer 22 takes the available individual data points (i.e., the patient's vital parameters) and supplies them to the specific algorithms. Subsequently, these algorithms compute the state of each part or regions 1 to 9 of the homunculus model 10 ("COMPUTE INDIVIDUAL HOMUNCULUS MODEL ANIMATIONS" in FIG. 8). The individual algorithms are described in detail below. Once the individual animations have been computed, they are passed to subroutine B (FIG. 9) of the overall visual patient monitoring algorithm.

Figure 8:
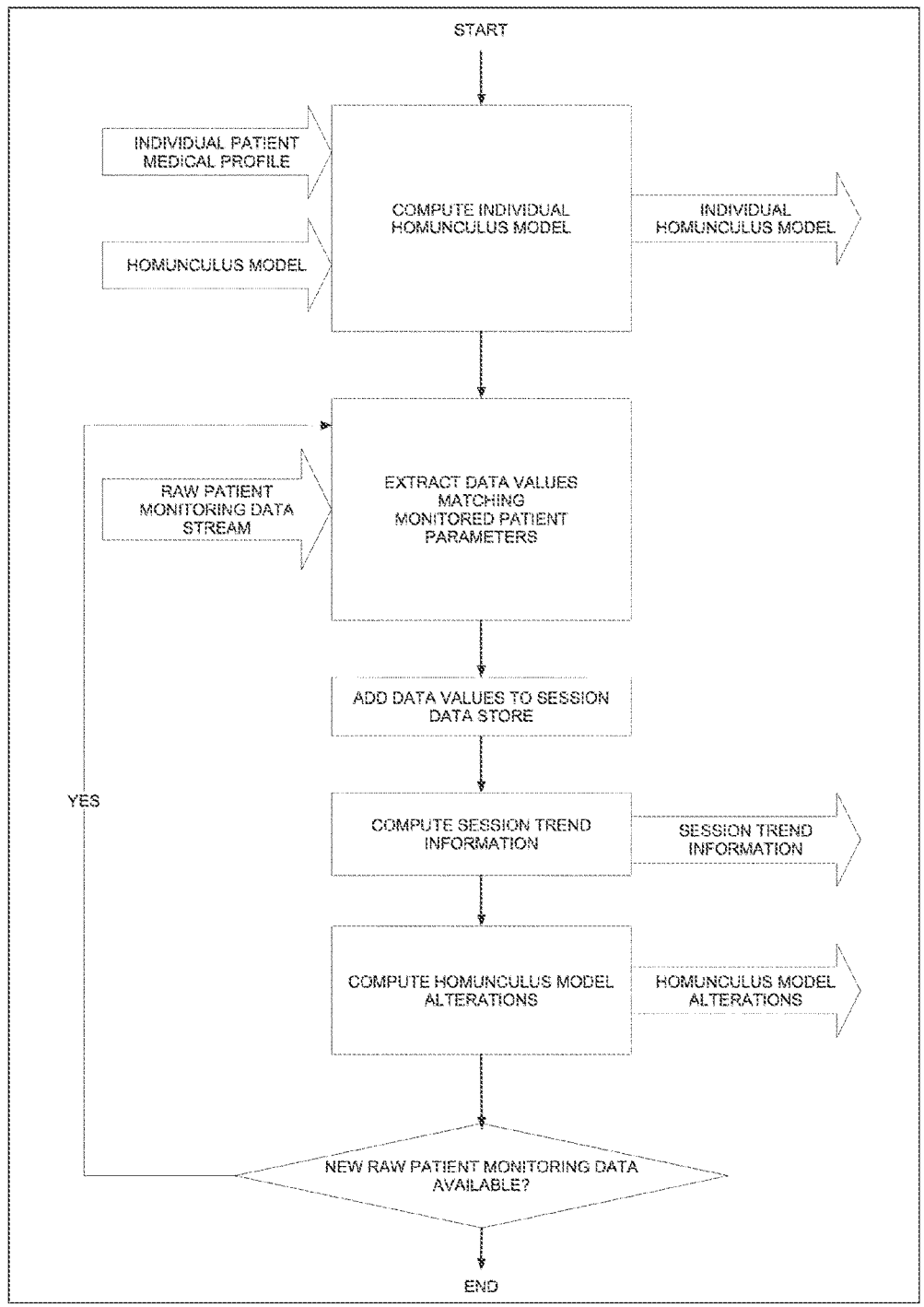
FIG. 8 is an illustration of a visual patient monitoring algorithm flow chart part 1 (Subroutine A).

Furthermore, when new patient monitoring data becomes available, the process starting from "EXTRACT DATA POINTS MATCHING MONITORED PATIENT PARAMETERS" in FIG. 8 is repeated until any more data can be extracted from the data stream.

Figure 9:
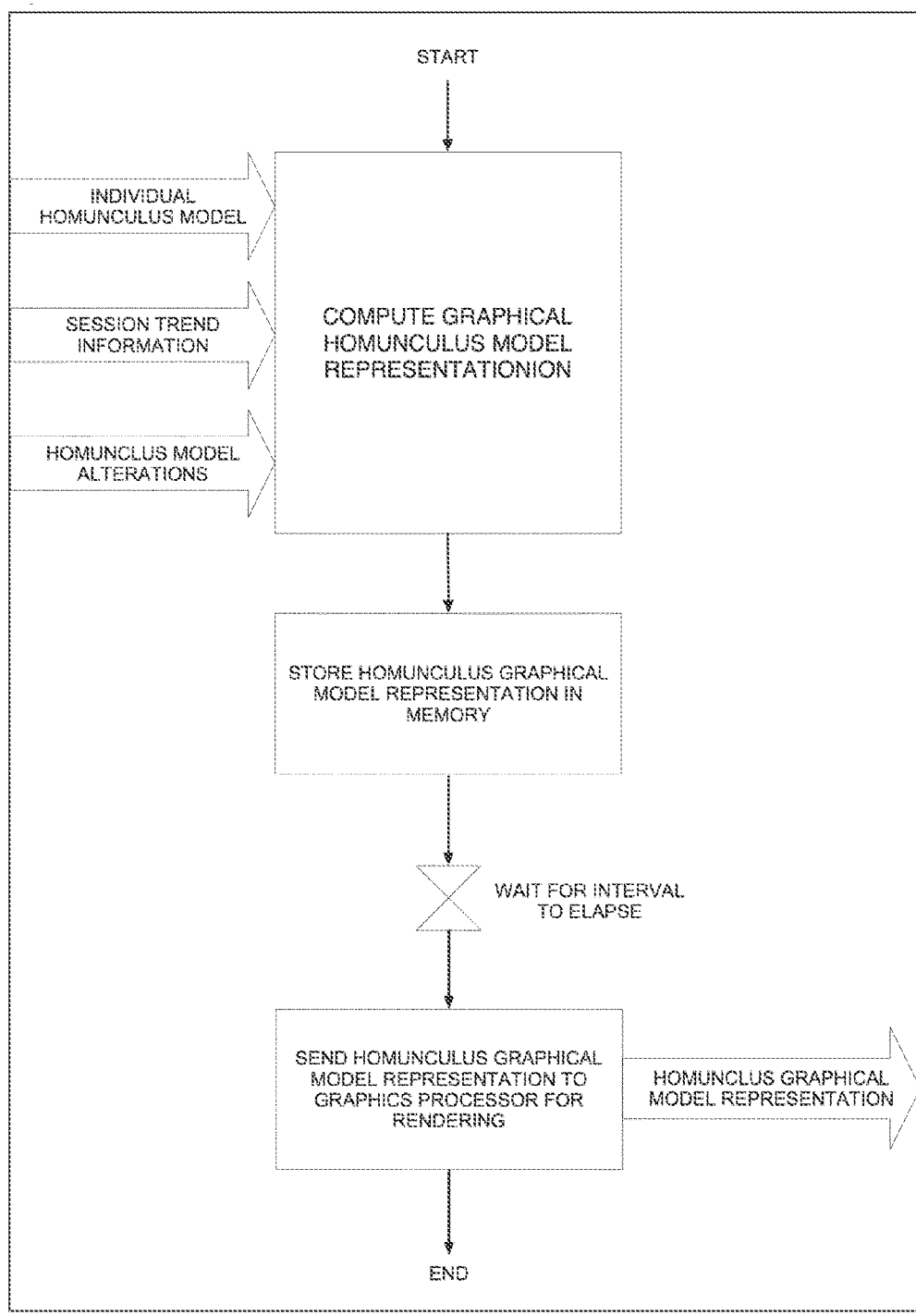
FIG. 9 is an illustration of a visual patient monitoring algorithm flow chart part 2 (Subroutine B).

FIG. 9 represents subroutine B of the visual patient monitoring overall algorithm (FIG. 5) according to an embodiment, in which subroutine A fills a data buffer in memory 23 that is loaded and consumed by subroutine B for further processing. In detail, the two- or three-dimensional homunculus model 10 is computed ("COMPUTE HOMUNCULUS GRAPHICAL MODEL REPRESENTATION" in FIG. 9) by using the individualized homunculus model (i.e., the customized patient avatar) 10, session trend information (i.e., the monitoring session history), and the model animations to be performed on the individual homunculus model 10.

Once the two- or three-dimensional representation of the homunculus 10 has been established, it is stored in memory 23 ("STORE HOMUNCULUS GRAPHICAL MODEL REPRESENTATION IN MEMORY") for later rendering by the graphics processor 21. In order to accommodate existing hardware limitations as imposed by the graphics processor 21, data stream, general purpose computer 22, or other involved components, the next step is to wait for a specific interval to be elapsed ("WAIT FOR INTERVAL TO ELAPSE" in FIG. 9) before sending the two- or three-dimensional model representation to the graphics processor 21 for rendering purposes. Hence, the latter timespan, which is pre- or dynamically determined, represents the sequence of image change by the display device 20 (i.e., the display refresh rate). Subroutine B is repeated as long as data is present in the data buffer filled by subroutine A.

The instructions for carrying out the present disclosure may be stored in any recordable medium such as a hard drive, magnetically recordable tape, or as a compact disk. They may be stored in the memory 23 (i.e., MEMORY in FIG. 5). The memory 23 may include both volatile and nonvolatile memory components. Volatile components are those that do not retain data upon loss of power. Nonvolatile components are those that retain data upon a loss of power.

Thus, the memory 23 may comprise, for example, random access memory (RAM), read-only memory (ROM), hard disk drives, solid state drives and/or other memory components, or a combination of any two or more of these memory components. The RAM may comprise, for example, static random access memory (SRAM), dynamic random access memory (DRAM), or magnetic random access memory (MRAM), non-volatile random-access memory (NVRAM), and other forms of memory. The ROM may comprise, for example, a programmable read-only memory (PROM), an erasable programmable read-only memory (EPROM), an electrically erasable programmable read-only memory (EEPROM), compact flash memory, or other like memory device.

In the following examples for the individual algorithms will be described.

Table 1a outlining which regions of the homunculus are affected by which data points, which attributes are altered according to algorithms #1-12.

| Region or part of homunculus | Affected by data point | Changed attributes | Name of algorithm |
| --- | --- | --- | --- |
| 1 (body) | Blood pressure (BP) | Volume or area of parts/regions (3D) or area (2D) | Visual patient monitoring algorithm #1 |
| | Pulse Rate SpO2 Sensor (PR) | Frequency of volume or area of parts/regions (3D) or area (2D) change | Visual patient monitoring algorithm #1 |
| | Oxygen saturation (SpO2) | Color change | Visual patient monitoring algorithm #2 |
| | Body Temperature (Temp) | Amount of temperature indicators | Visual patient monitoring algorithm #3 |
| 2 (visual heart) | Blood pressure (BP) | Volume/area | Visual patient monitoring algorithm #4 |
| | ECG QRS Heart Rate (HR) | Frequency of volume or area of parts/regions (3D) or area (2D) change | Visual patient monitoring algorithm #4 |
| | ECG ST-segment deflection (ST) | Color change of visual heart and reduction of pulsation dynamics in affected area | Visual patient monitoring algorithm #5 |
| | Right ventricular pressure (RVP) | Volume/area | Visual patient monitoring algorithm #6 |
| | ECG rhythm detection system (ECG) | Electrical conduction path form displayed (Visual electrical heart activity) | Visual patient monitoring Algorithm #7 |
| | Pulmonary capillary wedge pressure or wedge pressure (PCWP) | Volume/area | Visual patient monitoring algorithm #8 |
| | Mixed venous oxygen saturation (MVOS) | Color change | Visual patient monitoring algorithm #9 |
| | Cardiac output (CO)/ Cardiac index (CI) | Amount of cardiac output/cardiac index indicators displayed | Visual patient monitoring Algorithm #10 |
| 3 (visual arterial system) | Blood pressure (BP) | Volume/area | Visual patient monitoring Algorithm #11 |
| 4 (visual vena cava) | Central venous pressure (CVP) | Volume/area | Visual patient monitorting algorithm #12 |

Table 1b outlining which parts of the homunculus are affected by which data points, which attributes are altered according to algorithms #12-19.

| Part or region within homunculus | Affected by data point | Changed attributes | Name of algorithm |
| --- | --- | --- | --- |
| 5 (visual respiration, | Respiratory rate (RR) | Frequency of volume or area of | Visual patient monitoring algorithm # |

-continued

| Part or region within homunculus | Affected by data point | Changed attributes | Name of algorithm |
|---|---|---|---|
| visual lungs) | | parts/regions (3D) or area (2D) change | 13 |
| | Tidal volume (TV) | Volume/area | Visual patient monitoring algorithm # 13 |
| 6 (visual CO2 & Oxygen Cloud) | Respiratory rate (RR) | Frequency of volume or area of parts/regions (3D) or area (2D) change | Visual patient monitoring algorithm #14 |
| | Exspiratory carbondioxide measurement (eCO2) | Volume/area | Visual patient monitoring algorithm # 14 |
| | Expiratory oxygen measurement (eO2) | Volume/area | Visual patient monitoring algorithm #15 |
| 7 (eye(s) or visual brain activity) | Brain activity from e.g., Bispectral Index System (BIS), electroencephalogram (EEG) | Degree of openness of eyes Amount of brain activity indicators Facial expression of the homunculus | Visual patient monitoring algorithm #16 |
| 8 (visual Brain) | Intracranial pressure (ICP) | Appearance Amount of brain gyri and sulci, thickness of brain wall | Visual patient monitoring algorithm #17 |
| | Brain tissue oxygen tension (BO) | Color change | Visual patient monitoring algorithm #18 |
| 9 (hand(s) or visual neuromuscular transmission) | Neuromuscular transmission measurement system (NMT) | Degree of relaxation of hand muscles Relative position of selected parts/regions of body 1 of the homunculus 10. | Visual patient monitoring algorithm #19 |

Example 1: Visual Patient Monitoring Algorithm #1 (Pulse Rate and Blood Pressure)

This algorithm is used to make region 1 (body) as shown in FIG. 1 of the homunculus 10 pulsate in an intuitive way according to the pulse rate and blood pressure of the patient P. Here, the patient monitoring quantities (Inputs) are the Blood Pressure BP and the Pulse Rate PR e.g. from a SpO2 Sensor.

Figure 47:
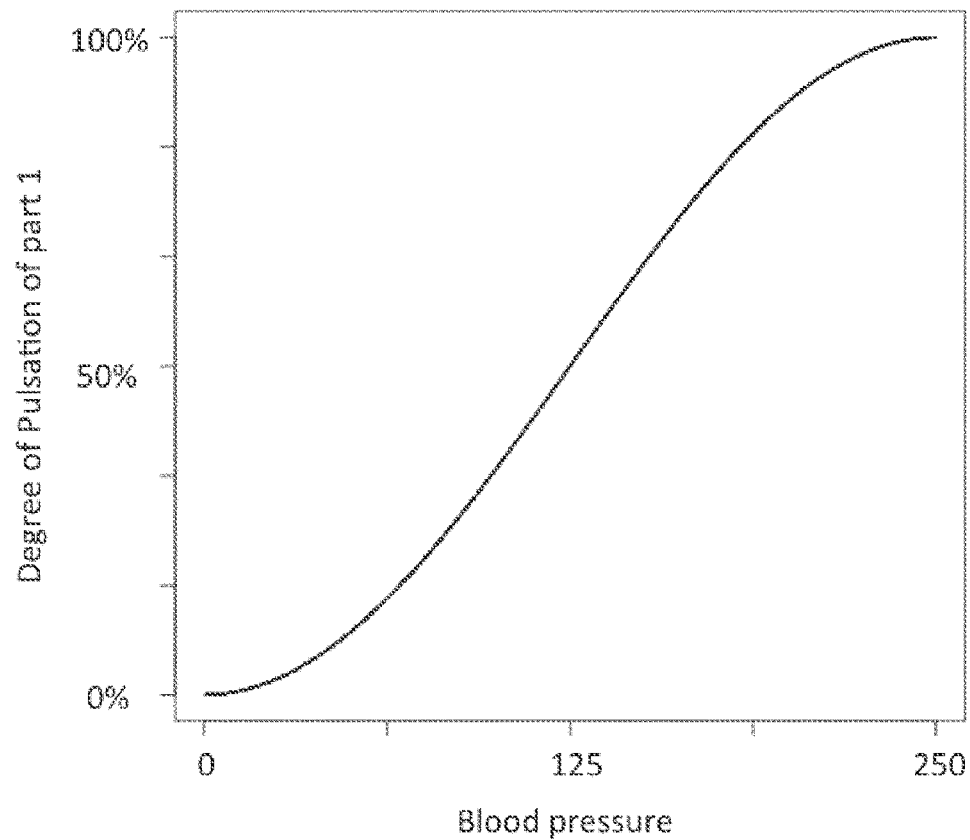
FIG. 47 is an illustration of pulsation of part (region) 1 over blood pressure.

Changes in input blood pressure BP lead to a change in volume or area of parts (3D) or area (2D) of region (body) 1 of the homunculus 10 particularly following an ease in ease out function (these functions are herein also denoted as smoothing functions, wherein FIG. 47 shows such a smoothing function that may be applied to the blood pressure, but may also be applied to other quantities). The ease in/out function causes very low and very high pressures to cause less extensive changes in volume or area of parts (3D) or area (2D) of region 1 when compared to changes in medium pressure ranges. This function will enable users to better detect low and high-pressure extremes. Region 1 of the homunculus 10 alternates between the volume or area of parts (3D) or area (2D) value of diastolic blood pressure (minimum) and systolic blood pressure (maximum). The changes in volume or area of parts (3D) or area (2D) of region 1 occurs with the frequency of the pulse rate PR, derived e.g. from the SpO2 sensor, and follows an arterial pressure curve form.

The arterial pressure curve form according to which the volume or area of parts (3D) or area (2D) change of region (body) 1 is achieved, is stored in memory 23. Several curve forms may be stored in memory 23 and displayed for different blood pressure amplitudes.

Figure 10:
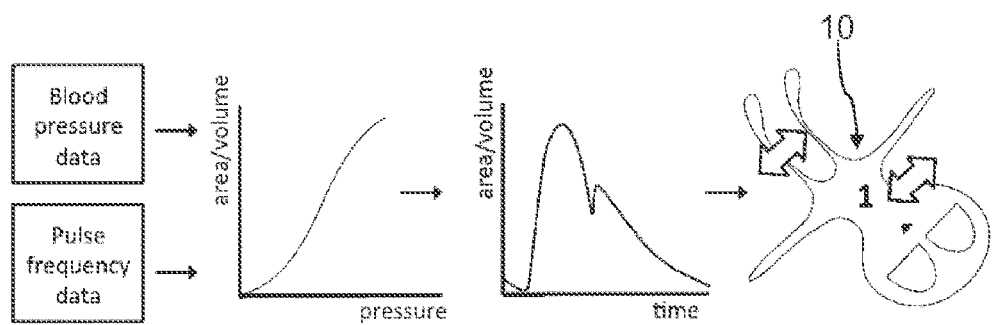
FIG. 10 is an illustration of a schematic overview of the logic of the visual patient monitoring algorithm #1 (pulse rate and blood pressure).
Figure 11:
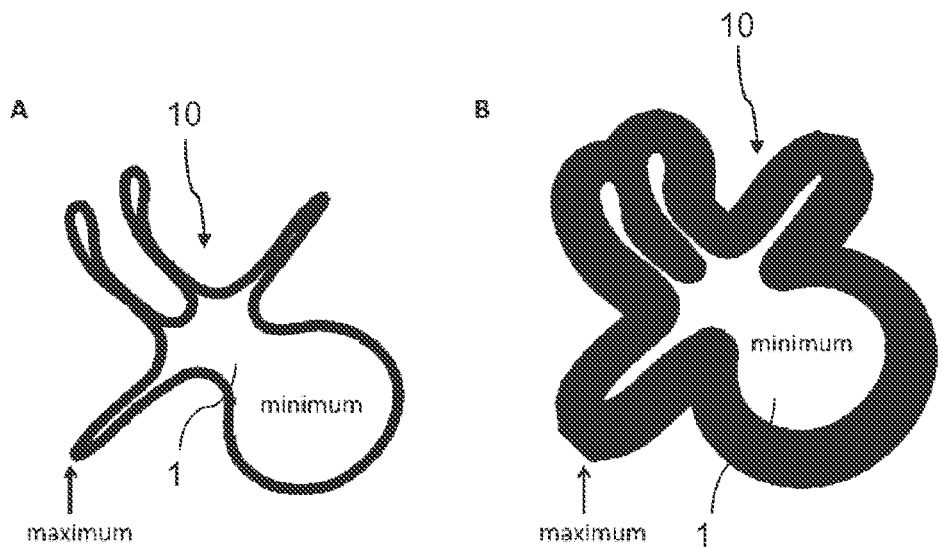
FIG. 11 is an illustration of graphical examples of changes in volume or area of parts (3D) or area (2D) of part 1 of the homunculus taking place during each cycle from minimum to maximum blood pressure, A: a slight change in area of part 1 as in low blood pressure, B: a larger change in area of part 1 as in high blood pressure.

The change in volume or area of parts (3D) or area (2D) of region (body) 1 behaves according to the actual arterial pressure curve input from the patient P, when this input is available. A schematic overview of this algorithm is given in FIG. 10. FIG. 11 provides a graphical example of a change in volume or area of parts (3D) or area (2D) of region (body) 1 of the homunculus 10 taking place during each cycle from minimum to maximum blood pressure.

Example 2: Visual Patient Monitoring Algorithm #2 (Visual Oxygen Saturation)

This algorithm allows region 1, i.e. the body 1 of the homunculus 10, to change its skin color in an intuitive way according to the oxygen saturation of the patient P. Here, the patient monitoring quantity (input) is the oxygen saturation e.g. from a SpO2 Sensor (SpO2).

Changes in the oxygen saturation lead to a change in color of body 1 of the homunculus 10. At 100% oxygen saturation, body 1 of the homunculus 10 has a normal skin color tone (e.g., HEX color #F8EFDA), representing the look of healthy skin at normal oxygen levels. As oxygen saturation decreases, body 1 gradually becomes light blue (e.g., HEX color #84B0E8) to dark blue (e.g., HEX color #0E3996) and finally purple (e.g., HEX color #723C7F) and grey (e.g., HEX color #DEDEDE) representing various degrees of hypoxia. Assigning other, different colors to the saturation data points will occur to those skilled in the art and may be used without varying from the spirit of this disclosure.

Figure 12:
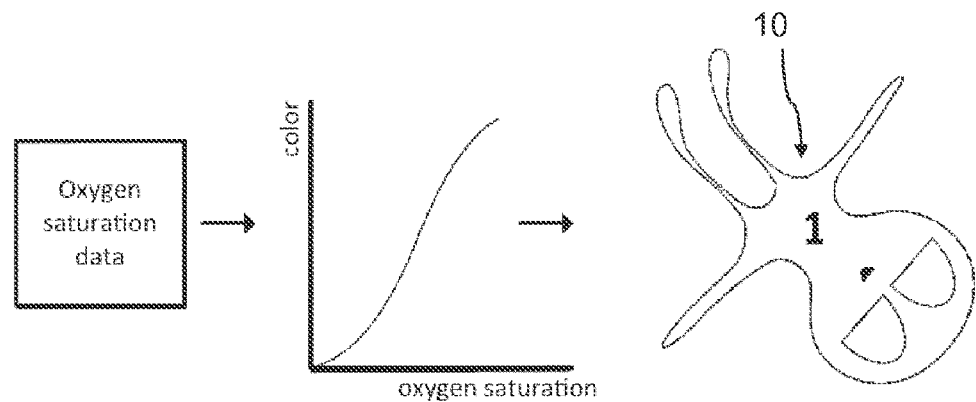
FIG. 12 is an illustration of a schematic overview of the logic of the visual patient monitoring algorithm #2 (oxygen saturation).
Figure 13:
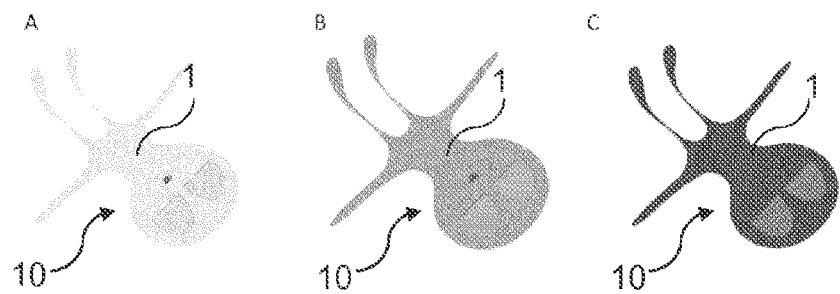
FIG. 13 is an illustration of graphical examples of the changes in color of part 1 of the homunculus according to oxygen saturation.

A schematic overview of this algorithm is given in FIG. 12. FIG. 13 provides graphical examples of the changes in color of body 1 of the homunculus 10 according to oxygen saturation data. Here, FIG. 13 shows graphical examples of changes in color (shown as grey scale) of body 1 of the homunculus 10 according to oxygen saturation. A: 100% oxygen saturation B: 90% oxygen saturation C: 75% oxygen saturation.

Example 3: Visual Patient Monitoring Algorithm #3
(Visual Patient Temperature)

This algorithm allows the patients temperature to be indicated in an intuitive way in body 1 (FIG. 1) of the homunculus 10 according to the temperature data of the patient P. Here, the corresponding patient monitoring quantity (input) is the body temperature BT.

Figure 14:
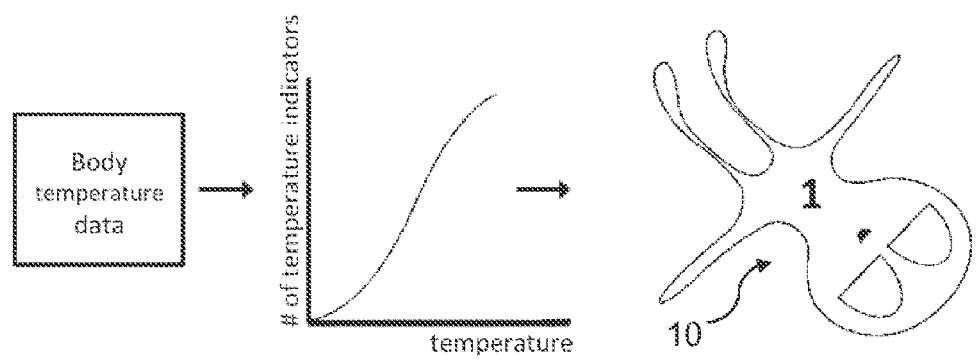
FIG. 14 is an illustration of a schematic overview of the logic of the visual patient monitoring algorithm #3 (body temperature).
Figure 15:
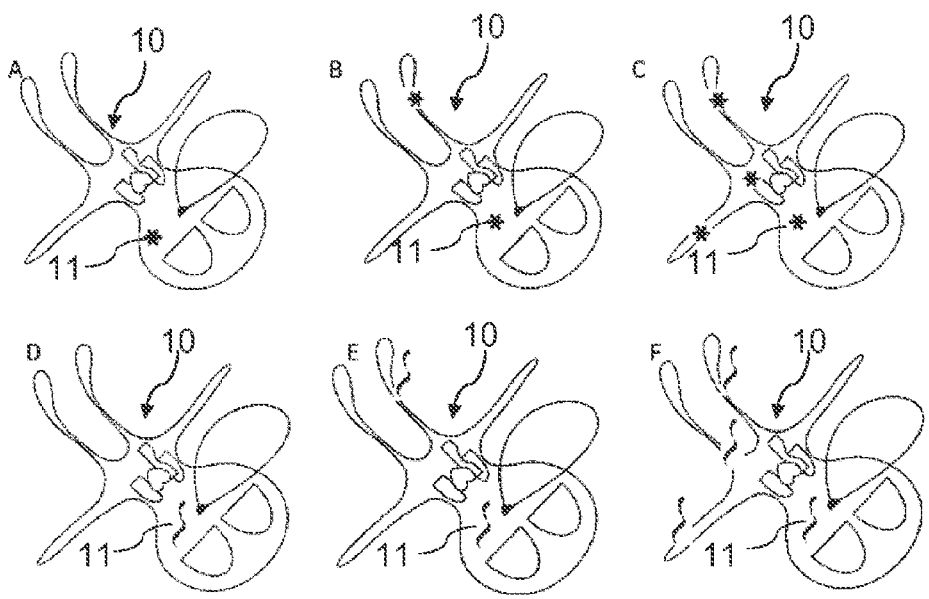
FIG. 15 is an illustration of graphical examples of the changes in the amount of temperature indicators displayed in part 1 of the homunculus according to body temperature.

According to the temperature data input, temperature indicators 11 appear on body 1 of the homunculus 10. The amount of temperature indicators 11 presented allows the user to understand the temperature of the patient P intuitively. Temperature indicators 11 for temperatures lower than normal may be icicles, snowflakes, temperature indicators 11 for temperatures higher than normal may be sweat pearls or heat waves rising from body 1 of the homunculus 10. The amount of temperature indicators 11 shown preferably follows an ease in/out function. This enables users to detect low and high-temperature extremes better. Assigning different designs of temperature indicators 11 than the ones described here as an embodiment of the disclosure, e.g. the appearance of sweat pearls or flames to indicate high temperature or a layer of snowflakes to indicate low temperature, will occur to those skilled in the art and may be used without varying from the spirit of this disclosure. A schematic overview of this algorithm is given in FIG. 14. FIG. 15 provides a graphical example of a change in the amount of temperature indicators 11 of body 1 of the homunculus 10 according to body temperature of the patient P. Here, FIG. 15 shows graphical examples of the changes in the amounts of temperature indicators 11 displayed in region (body) 1 of the homunculus 10 according to body temperature. A: 35.7 degrees Celsius, B: 35.3 degrees Celsius C: 34.5 degrees Celsius D: 37.0 degrees Celsius E: 37.5 degrees Celsius F: 39.5 degrees Celsius.

Example 4: Visual Patient Monitoring Algorithm #4
(Visual Heart)

This algorithm allows region 2, i.e. the heart of the homunculus 10 (FIG. 1), to pulsate in an intuitive way according to the ECG QRS heart rate and blood pressure of the patient. Here, correspondingly, the patient monitoring quantities (inputs) are the ECG QRS heart rate (HR) and Blood pressure (BP).

Changes in input blood pressure lead to a change in volume or area of parts (3D) or area (2D) of the heart 2 particularly following an ease in/out function. The ease in/out function causes very low and very high pressures to cause less extensive changes in volume or area of parts (3D) or area (2D) of heart 2 when compared to changes in medium pressure ranges. This function will enable users to better detect low and high-pressure extremes. Region (heart) 2 of the homunculus 10 alternates between the volume or area of parts (3D) or area (2D) value of diastolic blood pressure (minimum) and systolic blood pressure (maximum). The changes in volume or area of parts (3D) or area (2D) of region (heart) 2 occurs with the frequency of the ECG QRS heart rate (HR), and follows an arterial pressure curve form.

Figure 16:
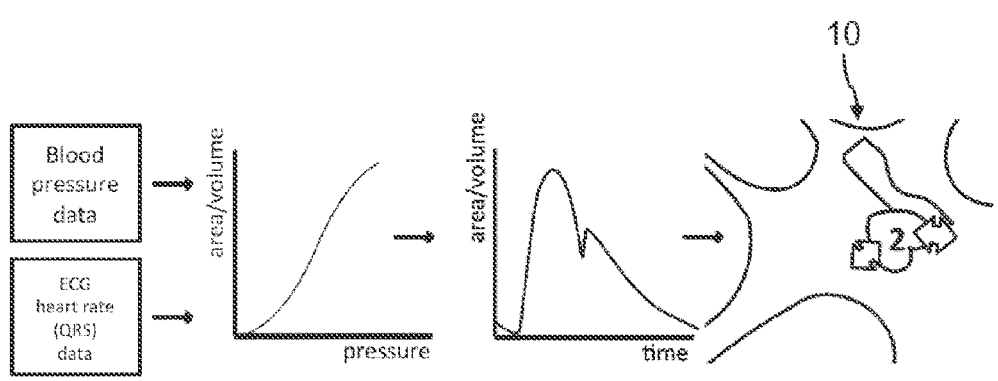
FIG. 16 is an illustration of a schematic overview of the logic of the visual patient monitoring algorithm #4 (ECG, QRS heart rate, blood pressure).

The arterial pressure curve form according to which the volume or area of parts (3D) or area (2D) change of region (heart) 2 is achieved, is stored in memory 23. A schematic overview of this algorithm is given in FIG. 16.

Example 5: Visual Patient Monitoring Algorithm #5
(Visual ST-Segment Deflection)

Inputs: ECG QRS heart rate HR and Blood pressure BP, ST-Segments of leads aVF, aVR, aVL, V1, V2, V3, V4, V5, V6.

This algorithm allows for specific sections of the heart 2 (FIG. 1) of the homunculus 10 to change their color and reduce the dynamics of their movement according to ST-segment deflection input from the ECG leads. An intuitive color will be chosen to make the muscle of the visual heart 2 appear hypoxic, e.g., a darker shade of red. In addition to the color change, in the specified parts of heart 2 of the homunculus 10 also the movement (dynamic change of area/volume) is reduced. These alterations, i.e., changes in color and reduction in movement represent various degrees of ST-segment deflection and underlying suggested heart muscle hypoxia or ischemia.

ST-segment deflections lead to a change in color of specific sections of heart 2 of the homunculus 10. At zero ST-segment deflection the sections of heart 2 of the homunculus 10 have a normal, default red color tone (e.g., HEX color #FF5555), representing the look of a healthy heart muscle at normal oxygen levels. As ST-segment deflection increases in one or more ECG leads, the sections of heart 2 of the homunculus 10 allocated to the ECG lead gradually become darker, e.g., from HEX color #C90000 to HEX color #8B0000 and finally purple (e.g., HEX color #723C7F) and grey (e.g., HEX color #DEDEDE). Assigning other, different colors to the ST-segment deflection data points will occur to those skilled in the art and may be used without varying from the spirit of this disclosure.

For example, an ST-segment deflection in leads representing the septal part of the heart 2 (i.e., leads V1, V2) will cause color changes and reduction of area/volume change (i.e., less dynamic movement) of the septal part of heart 2 of the homunculus 10. Likewise, an ST-segment deflection in leads representing the inferior part of the heart 2 (i.e., leads II, III, aVF) will cause color changes and less dynamic movement of the inferior part of heart 2 of the homunculus 10.

Changes in ST-segment deflection of specific ECG leads (e.g., V1, V2, v3), leads to a change in volume or area of parts (3D) or area (2D) of the sections of heart 2 of the homunculus 10 allocated to these ECG leads. The ease in/out function causes very small and very large ST-segment deflections to cause less extensive changes in volume or area of parts (3D) or area (2D) of heart 2 when compared to changes in medium ST-segment deflection ranges. This function will enable users to better detect relevant ST-segment deflections.

Figure 17:
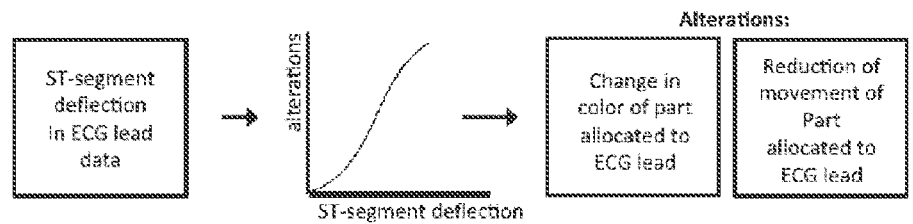
FIG. 17 is an illustration of a schematic overview of the logic of the visual patient monitoring algorithm #5 (ST-segment deflection).

FIG. 17 gives a schematic overview of this algorithm.

Figure 18:
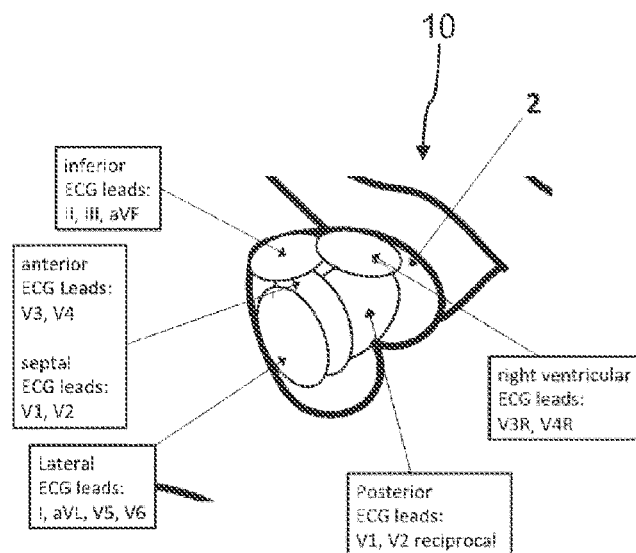
FIG. 18 is an illustration of graphical examples of possible allocations of the ECG leads to specific sections of part 2 of the homunculus according to ST-segment deflection data.

Examples of allocations of leads to parts of the visual heart 2 according to an embodiment are given in FIG. 18.

Figure 19:
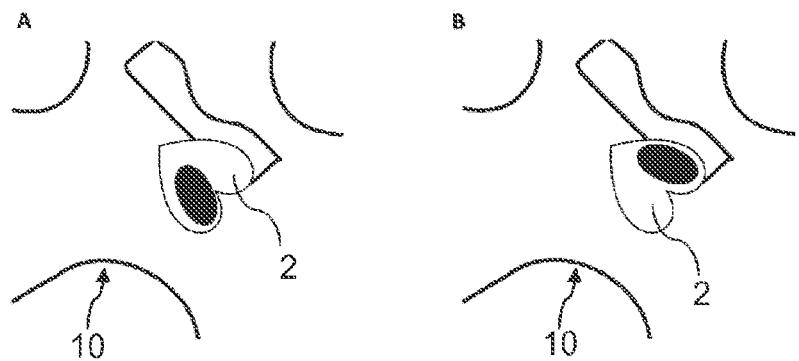
FIG. 19 is an illustration of graphical examples of the change in color of specified sections of part 2 of the homunculus according to ST-segment deflection data.

FIG. 19 provides graphical examples of ST-segment deflections in specific ECG leads. Here, FIG. 19 shows graphical examples of the changes in color of specified sections of the heart 2 of the homunculus 10 according to ST-segment deflection data. A: ST-segment deflection in anterior ECG leads (i.e., V3, V4) B: ST-segment deflection in right ventricular ECG leads (i.e., V3R, V4R). According to the ST-segment deflection algorithm in addition to the color change in the specified parts of heart 2 of the homunculus 10 also the movement (dynamic change of area/volume) is reduced.

Example 6: Visual Patient Monitoring Algorithm #6 (Visual Right Ventricular Pressure)

This algorithm allows for a specific section of heart 2 (e.g. FIG. 1) of the homunculus 10 to change its volume or area of parts (3D) or area (2D) in an intuitive way according to the right ventricular pressure of the patient P. Here, the patient monitoring quantity (inputs) is the Right ventricular pressure (RVP).

Figure 20:
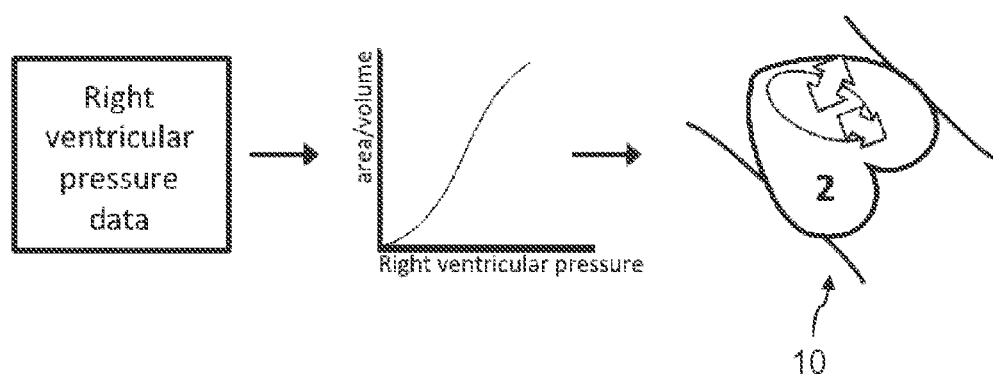
FIG. 20 is an illustration of a schematic overview of the logic of the visual patient monitoring algorithm #6 (right ventricular pressure).

Changes in input right ventricular pressure lead to a change in volume or area of parts (3D) or area (2D) of a specific section of heart 2 of the homunculus 10, representing the right ventricle of the heart 2, particularly following an ease in/out function. The ease in/out function causes very low and very high pressures to cause less extensive changes in volume or area of parts (3D) or area (2D) of the specified section of heart 2 when compared to changes in medium pressure ranges. This function will enable users better to detect low and high extremes of right ventricular pressure. The volume or area of parts (3D) or area (2D) of the specific part of the homunculus 10 fluctuates according to the right ventricular pressure wave, when this input is available. FIG. 20 gives a schematic overview of this algorithm.

Example 7: Visual Patient Monitoring Algorithm #7 (Visual Electrical Heart Activity)

This algorithm is used to enable heart 2 of the homunculus 10 (e.g. FIG. 1) to show the heart rhythm of the patient P as detected by a rhythm detection software in an intuitive way.

The detection of specific heart rhythms (i.e., electrical heart activity) causes the display of electrical conduction path forms 14 associated with the detected rhythm on part 2 of the homunculus 10.

Figure 21:
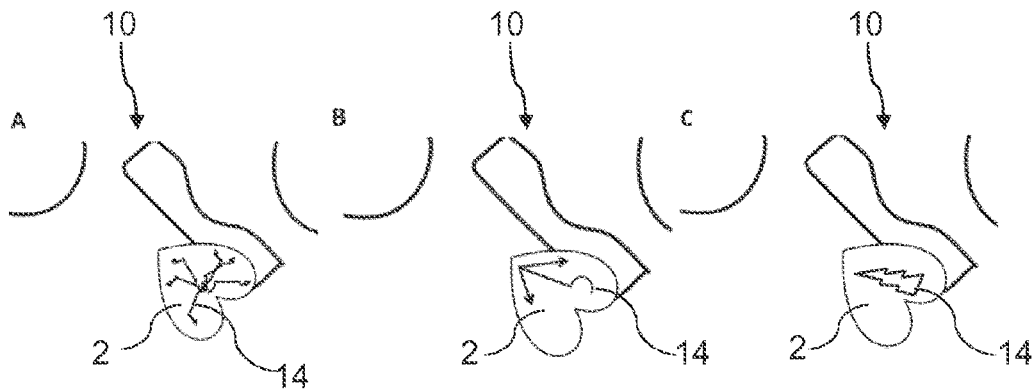
FIG. 21 is an illustration of graphical examples of electrical conduction path forms (i.e., electrical heart activity) displayed on part 2 of the homunculus according to ECG rhythms detected by an ECG rhythm detection system.

The electrical conduction paths forms 14, which are displayed according to the detected heart rhythm, are stored in memory 23. Several conduction path forms 15 may be stored in memory 23 and displayed for different ECG heart rhythms. FIG. 21 shows graphical examples of various electrical conduction path forms 14 displayed on heart 2 of the homunculus 10 according to ECG rhythms detected by ECG rhythm detection. A: ventricular fibrilation, B: regular sinus rhythm, C: Pacemakerrhythm.

Example 8: Visual Patient Monitoring Algorithm #8 (Visual Pulmonary Capillary Wedge Pressure or Wedge Pressure)

This algorithm allows for a specific section of heart 2 (e.g. FIG. 1) of the homunculus 10 to change its volume or area of parts (3D) or area (2D) in an intuitive way according to the pulmonary capillary wedge pressure of the patient P. Pulmonary capillary wedge pressure is also known as wedge pressure. Here, the patient monitoring quantities (inputs) are the pulmonary capillary wedge pressure or wedge pressure (PCWP).

Figure 22:
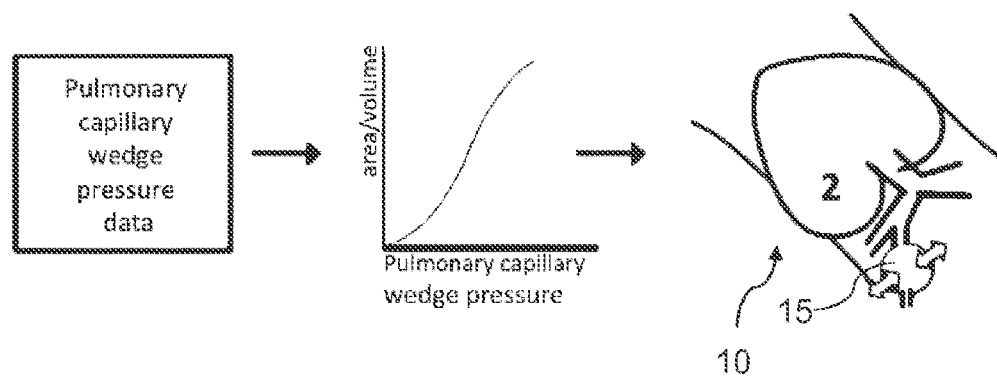
FIG. 22 is an illustration of a schematic overview of the logic of the visual patient monitoring algorithm #7 (pulmonary capillary wedge pressure).
Figure 23:
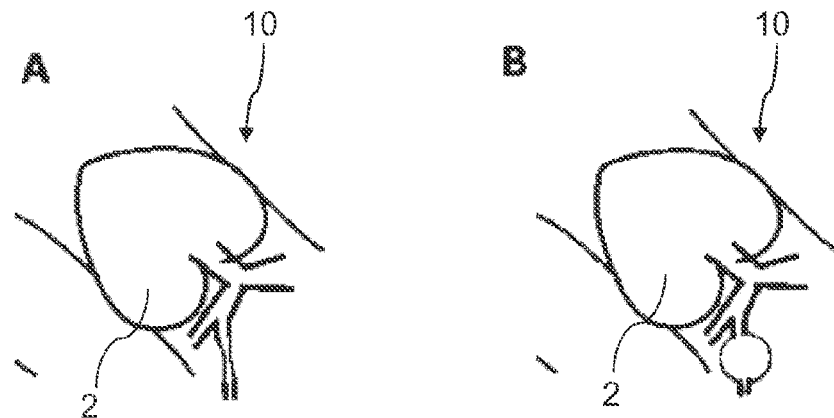
FIG. 23 is an illustration of graphical examples of the change in area/volume of a specific section of part 2 of the homunculus according to pulmonary capillary wedge pressure.

Changes in input pulmonary capillary wedge pressure lead to a change in volume or area of parts (3D) or area (2D) of a specific section of heart 2 of the homunculus 10, representing a section 15 of the pulmonary artery, particularly following an ease in/out function. The ease in/out function causes very low and very high pressures to cause less extensive changes in volume or area of parts (3D) or area (2D) of the specified section of heart 2 when compared to changes in medium pressure ranges. This function will enable users better to detect low and high extremes of pulmonary capillary wedge pressure. The volume or area of parts (3D) or area (2D) of the specific part 15 of the homunculus 10 fluctuates according to the pulmonary artery pressure wave, when this input is available. A schematic overview of this algorithm is given in FIG. 22. FIG. 23 provides graphical examples of different pulmonary capillary wedge pressures.

Example 9: Visual Patient Monitoring Algorithm #9 (Visual Mixed Venous Oxygen Saturation)

This algorithm allows a specific section of part 2 of the homunculus (FIG. 1) of the homunculus 10 to change its color in an intuitive way according to the mixed venous oxygen saturation of the patient P. Here, the patient monitoring quantity (input) is the mixed venous oxygen saturation (MVOS).

Changes in the mixed venous oxygen saturation lead to a change in color of a specific section of heart 2 of the homunculus 10, representing the blood inside the right ventricle of the heart 2. At 80% mixed venous oxygen saturation, the specific section of heart 2 of the homunculus 10 has an intuitive light blue color (e.g., HEX color #84B0E8) representing high mixed venous oxygen content. As oxygen content decreases the color gradually becomes darker (e.g., HEX color #0E3996) and eventually turns purple (e.g., HEX color #723C7F) and grey (e.g., HEX color #DEDEDE) representing various degrees of mixed venous hypoxia. Assigning other, different colors to the mixed venous saturation data points will occur to those skilled in the art and may be used without varying from the spirit of this disclosure.

Figure 24:
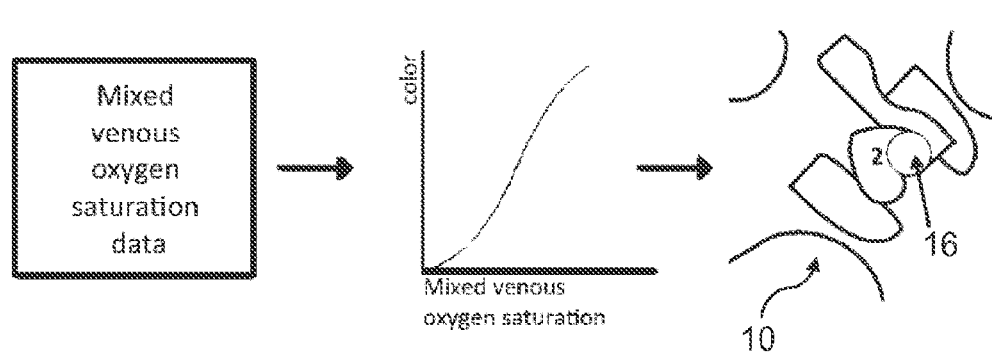
FIG. 24 is an illustration of a schematic overview of the logic of the visual patient monitoring algorithm #8 (visual mixed venous oxygen saturation).
Figure 25:
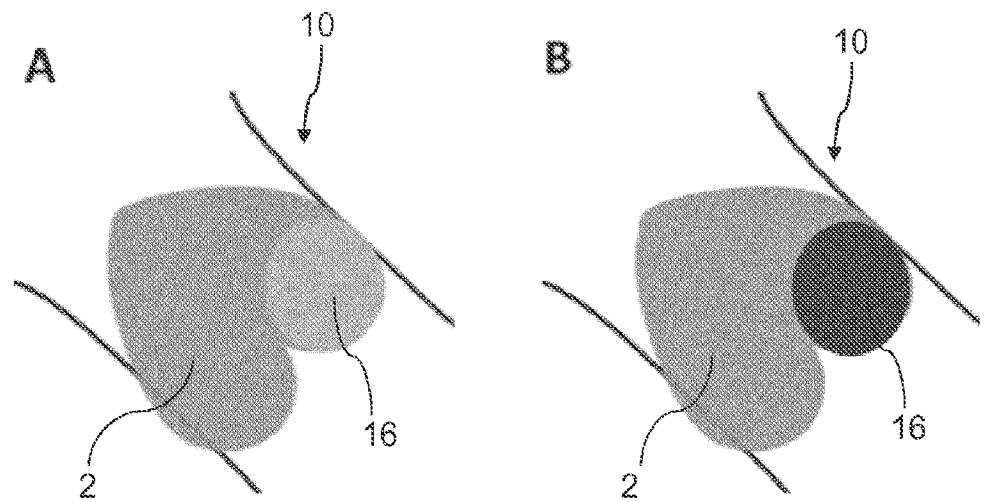
FIG. 25 is an illustration of graphical examples of the change in color of specified sections of part 2 of the homunculus according to mixed venous oxygen saturation.

The changes in color from light blue to dark blue and eventually grey particularly follow an ease in/out function. This function will enable users better to detect low and high mixed venous oxygen saturation extremes. A schematic overview of this algorithm is given in FIG. 24. FIG. 25 provides a graphical example of a change in color (here indicated in grey scale) of the specific section 16 of heart 2 of the homunculus 10 according to mixed venous oxygen saturation.

Example 10: Visual Patient Monitoring Algorithm #10 (Visual Cardiac Output, Visual Cardiac Index)

This algorithm allows the patients cardiac output, or cardiac index, which is the cardiac output related to body surface area, to be indicated in an intuitive way in heart 2 (e.g. FIG. 1) of the homunculus 10 according to the cardiac output or cardiac index measurement. Here, the patient monitoring quantity (input) is the cardiac output and/or cardiac index.

Figure 26:
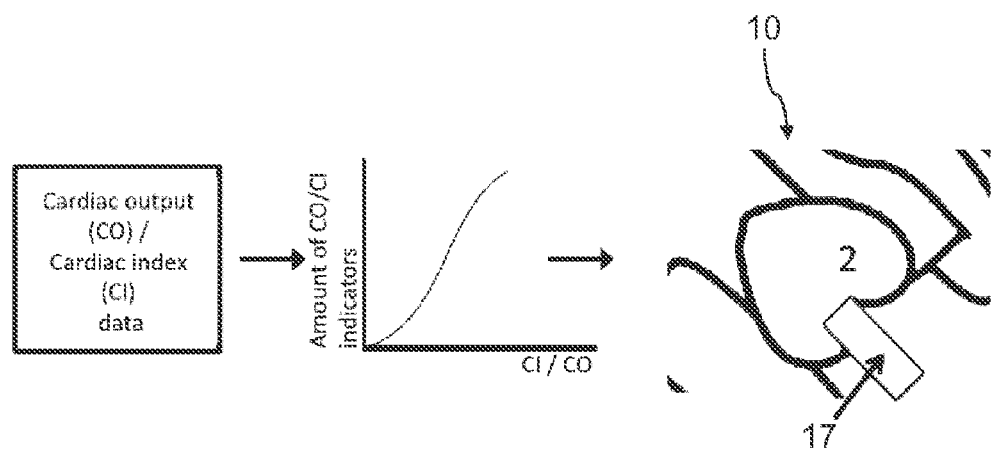
FIG. 26 is an illustration of a schematic overview of the logic of the visual patient monitoring algorithm #9 (cardiac output/cardiac index).
Figure 27:
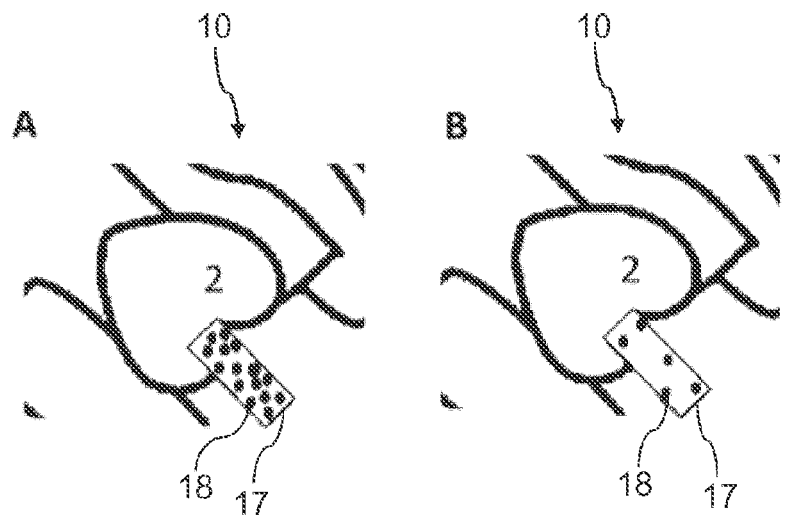
FIG. 27 is an illustration of graphical examples of the changes in the amounts of cardiac output indicators displayed in a specific section of part 2 of the homunculus according to cardiac output.

According to the cardiac output or cardiac index input, cardiac output indicators 18 appear on a specific section 17 of heart 2 of the homunculus 10. The amount of cardiac output indicators 18 presented allows the user to understand the cardiac output of the patient P intuitively. Cardiac output or cardiac index indicators 18 include the amount of erythrocytes (red blood cells) being ejected from the left ventricle of the heart 2 into the aorta. The amount of cardiac output indicators 18 shown particularly follows an ease in/out function. This enables users to detect low and high cardiac output or cardiac index extremes better. Assigning different designs of cardiac output, respectively, cardiac index indicators 18 other than the red blood cells design described here as an embodiment of the disclosure, will occur to those skilled in the art and may be used without varying from the spirit of this disclosure. A schematic overview of this algorithm is given in FIG. 26. FIG. 27 provides a graphical example of a change in the amount of cardiac output indicators 18 shown in a specific section 17 of heart 2 of the homunculus 10 according to cardiac output or cardiac index measurement. Here, FIG. 27 shows graphical examples of the changes in the amounts of cardiac output indicators displayed in a specific section of part 2 of the homunculus according to cardiac output. A: Cardiac output of 5 L/min B: cardiac output of 2.5 L/min.

Example 11: Visual Patient Monitoring Algorithm #11 (Visual Arterial System)

This algorithm is used to enable region 3 in form of visual arteries (or artery system) of the homunculus 10 (e.g. FIG. 1) pulsate in an intuitive way according to the pulse rate or invasive (art.) blood pressure wave and blood pressure of the patient P. Here, the patient monitoring quantities (inputs) are the blood pressure BP and the pulse rate e.g. from a SpO2 Sensor (PR) or from an invasive blood pressure wave.

Changes in input blood pressure lead to a change in volume or area of parts (3D) or area (2D) of region 3 of the homunculus 10 particularly following an ease in ease out function. The ease in/out function causes very low and very high pressures to cause less extensive changes in volume or area of parts (3D) or area (2D) of part 3 when compared to changes in medium pressure ranges. This function will enable users to better detect low and high-pressure extremes. Regions 3 of the homunculus 10 alternate between the volume or area of parts (3D) or area (2D) value of diastolic blood pressure (minimum) and systolic blood pressure (maximum). The changes in volume or area of parts (3D) or area (2D) of region 3 occur with the frequency of the pulse rate (PR), derived from the e.g. SpO2 sensor or from e.g. an invasive blood pressure wave, and follow an arterial pressure curve form.

The arterial pressure curve form according to which the volume or area of parts (3D) or area (2D) change of part 3 is achieved, is stored in memory 23. Several curve forms may be stored in memory 23 and displayed for different blood pressure amplitudes.

Figure 28:
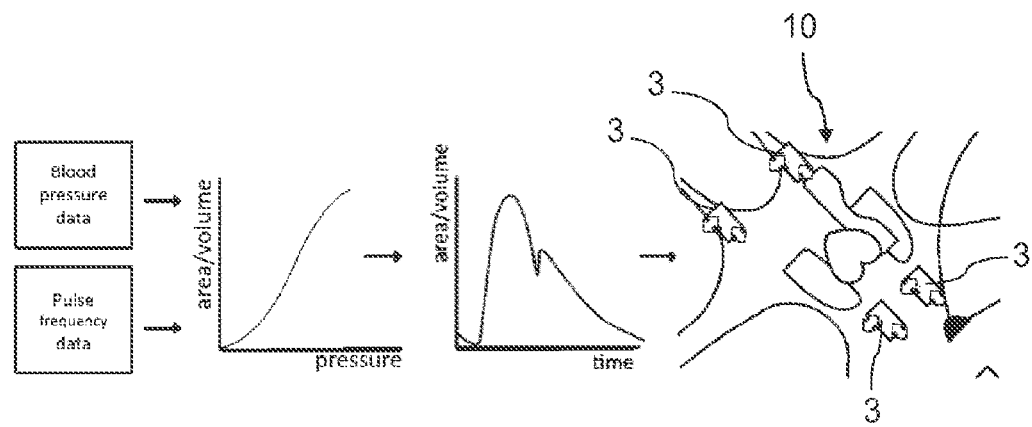
FIG. 28 is an illustration of a schematic overview of the logic of the visual patient monitoring algorithm #11 (blood pressure, pulse rate from SpO2 sensor or invasive blood pressure wave).
Figure 29:
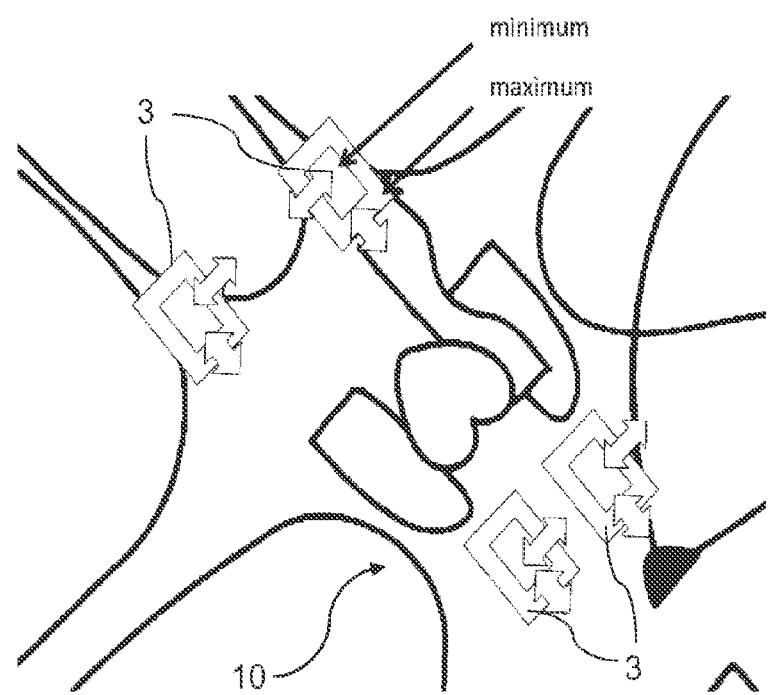
FIG. 29 is an illustration of a graphical example of a change in volume or area of parts (3D) or area (2D) of part 3 of the homunculus taking place during each cycle from minimum to maximum blood pressure.

The change in volume or area of parts (3D) or area (2D) of region 3 of the homunculus 10 behaves according to the actual arterial pressure curve input from the patient P, when this input is available. FIG. 28 gives a schematic overview of this algorithm. FIG. 29 provides a graphical example of a change in volume or area of parts (3D) or area (2D) of regions 3 of the homunculus 10 taking place during each cycle from minimum to maximum blood pressure.

Example 12: Visual Patient Monitoring Algorithm #12 (Visual Vena Cava)

This algorithm allows region 4 (FIG. 1) of the homunculus 10, i.e., the vena cava 4, to change its volume or area of parts (3D) or area (2D) in an intuitive way according to the central venous pressure of the patient P. Here, the patient monitoring quantity (inputs) is the central venous pressure (CVP).

Figure 30:
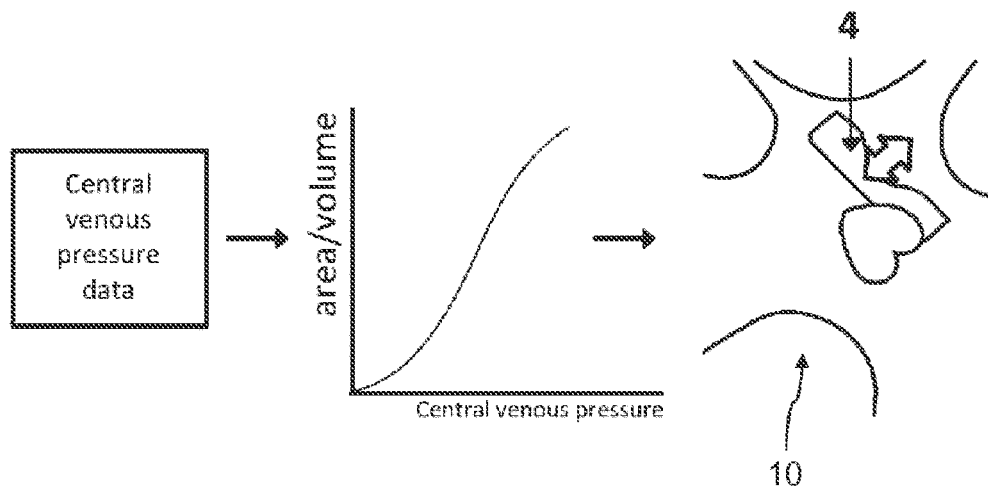
FIG. 30 is an illustration of a schematic overview of the logic of the visual patient monitoring algorithm #12 (central venous pressure).

Changes in input central venous pressure lead to a change in volume or area of parts (3D) or area (2D) of the vena cava 4 particularly following an ease in/out function. The ease in/out function causes very low and very high pressures to cause less extensive changes in volume or area of parts (3D) or area (2D) of region 4 when compared to changes in medium pressure ranges. This function will enable users better to detect low and high extremes of central venous pressure. The volume or area of parts (3D) or area (2D) of region (vena cava) 4 of the homunculus 10 fluctuate according to the CVP pressure wave, when this input is available. A schematic overview of this algorithm is given in FIG. 30.

Example 13: Visual Patient Algorithm #13 (Visual Respiration)

This algorithm allows regions 5 (e.g. FIG. 1) that represent the two lungs of the homunculus 10 to change their volume or area of parts (3D) or area (2D) in an intuitive way according to the respiratory rate RR and tidal volume TV. Here, the patient monitoring quantities (inputs) are the respiratory rate (RR) and the tidal volume TV.

Figure 31:
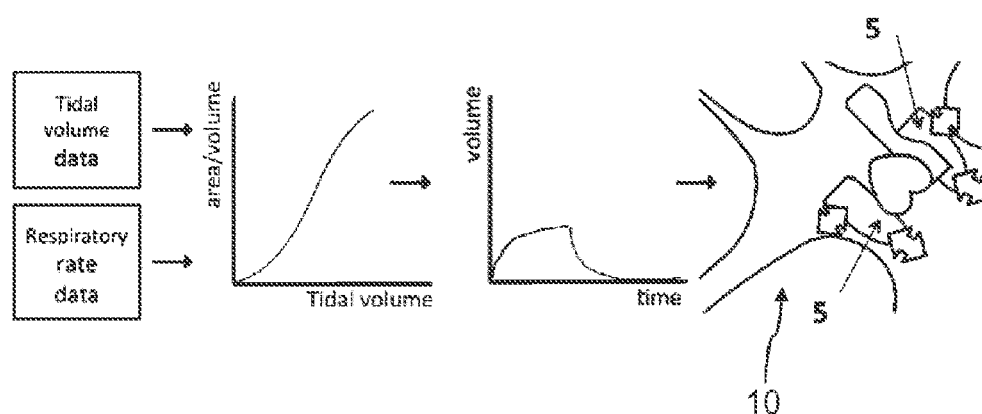
FIG. 31 is an illustration of a schematic overview of the logic of the visual patient monitoring algorithm #13 (respiratory rate and tidal volume).

Changes in input tidal volume TV lead to a change in volume or area of parts (3D) or area (2D) of both regions 5 particularly following an ease in ease out function. The ease in/out function causes very low and very high tidal volumes to cause less extensive changes in volume or area of parts (3D) or area (2D) of regions (lungs) 5 when compared to changes in medium tidal volume ranges. This function will enable users better to detect low and high tidal volume extremes. Regions (lungs) 5 of the homunculus 10 alternate between a default volume or area of parts (3D) or area (2D) value (minimum) and the value according to the tidal value of the patient P (maximum). The changes in volume or area of parts (3D) or area (2D) of both lungs in part 5 occur with the frequency of the respiratory rate PR, and preferably follows a volume-time curve. The volume time curve according to which the volume or area of parts (3D) or area (2D) change of both lungs 5 is achieved, is stored in memory 23. Several curve forms may be stored in memory 23 and displayed for different respiratory rates. The change in volume or area of parts (3D) or area (2D) of both lungs 5 is according to the actual volume or area of parts (3D) or area (2D) curve input from the patient P, when this input is available. FIG. 31 gives a schematic overview of this algorithm.

Example 14: Visual Patient Monitoring Algorithm #14 (Visual CO2 Cloud)

This algorithm allows a region 6 in the form of a CO2 cloud of the homunculus 10 (e.g. FIG. 1) to change its volume or area of parts (3D) or area (2D) in an intuitive way according to the respiratory rate RR and expiratory carbon dioxide measurement (eCO2). Here, the patient monitoring quantities (inputs) are the respiratory rate RR and expiratory carbon dioxide measurement eCO2.

Figure 32:
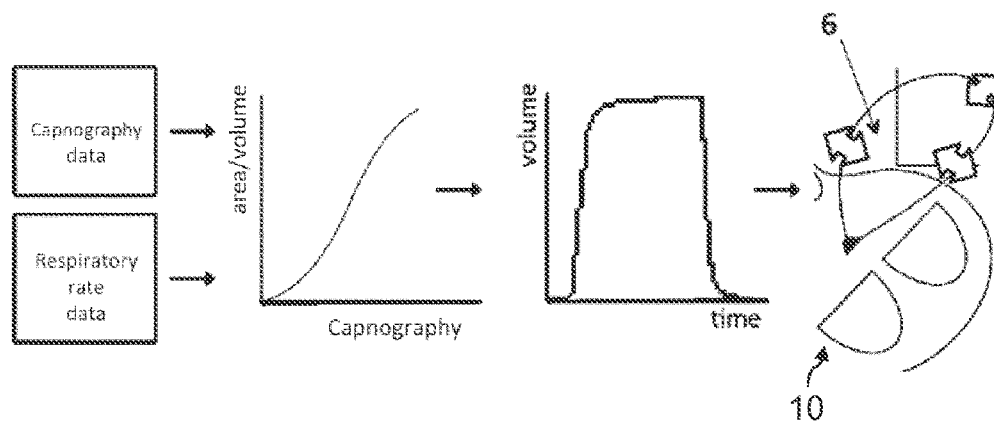
FIG. 32 is an illustration of a schematic overview of the logic of the visual patient monitoring algorithm #14 (respiratory rate and expiratory carbon dioxide).

Changes in input expiratory carbon dioxide measurement (eCO2) measurement (end-tidal CO2) (eCO2) leads to a change in volume or area of parts (3D) or area (2D) of region 6 particularly following an ease in ease out function. An intuitive color to represent carbon dioxide for region 6 of the homunculus 10 representing the CO2 cloud can be for example HEX color #F9FB04. The ease in/out function causes very low and very high end-expiratory CO2 values to cause less extensive changes in volume or area of parts (3D) or area (2D) of region 6 when compared to changes in medium end-tidal CO2 measurement. This function will enable users to better detect low and high end-tidal CO2 extremes. Region 6 of the homunculus 10 alternates between nonexistent (minimum) and the value according to the end-expiratory CO2 measurement of the patient P (maximum). The changes in volume or area of parts (3D) or area (2D) of region 6 occur with the frequency of the respiratory rate PR, and particularly follows an expiratory CO2 curve. The end-expiratory CO2 curve according to which the volume or area of parts (3D) or area (2D) change of region 6 is achieved, is stored in a memory. The change in volume or area of parts (3D) or area (2D) of region 6 behave according to the actual end-expiratory CO2 curve input (capnogaphy) from the patient P, when this input is available. Assigning other indicators different in design to the ones described here will occur to those skilled in the art and may be used without varying from the spirit of this disclosure. E.g., using the display of fewer or more expired gas bubbles to indicate the value of the end-expiratory CO2 value. FIG. 32 gives a schematic overview of this algorithm.

Example 15: Visual Patient Monitoring Algorithm #15 (Visual Oxygen Cloud)

This algorithm allows the fraction of expired oxygen (FeO2) to be indicated in an intuitive way in region 6 of the homunculus 10 (e.g. FIG. 1) according to the FeO2 data input. Here, the patient monitoring quantity (input) is the expired oxygen (FeO2).

Figure 33:
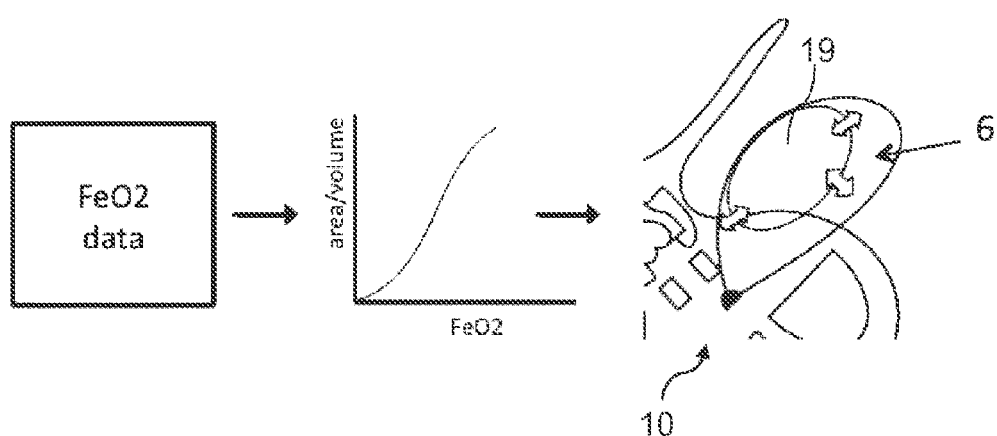
FIG. 33 is an illustration of a schematic overview of the logic of the visual patient monitoring algorithm #14 (expired oxygen concentration).
Figure 34:
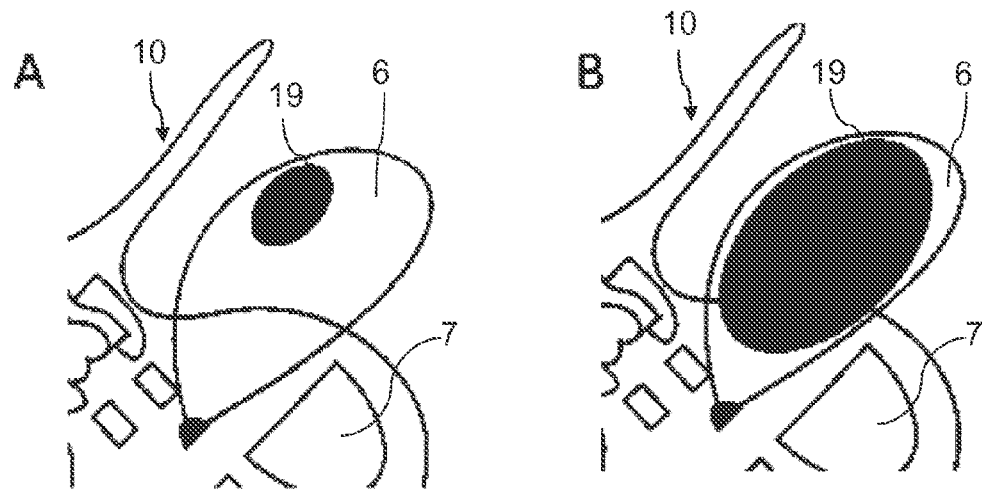
FIG. 34 is an illustration of graphical examples of the change in area/volume of a specific section of part 6 of the homunculus according to expired oxygen concentration.

Changes in the input expiratory oxygen (FeO2) lead to a change area/volume of a colored section 19 in region 6 of the homunculus 10 (visual CO2 & oxygen cloud) particularly following an ease in ease out function. The area[2D]/volume [3D] change will be relative to the dynamic area[2D]/volume[3D] changes of region 6 of the homunculus 10 occurring according to the visual patient monitoring algorithm #13 (visual respiration). An intuitive color to represent oxygen for the section 19 of region 6 representing expired oxygen can be for example HEX color #84B0E8. The ease in/out function causes very low and very high expiratory oxygen values to cause less extensive changes in volume or area of parts (3D) or area (2D) of the colored section 19 in region (e.g. cloud) 6 of the homunculus 10 when compared to changes in medium expiratory oxygen measurement. This function will enable users to better detect low and high FeO2 extremes. The colored section 19 in region 6 of the homunculus 10 alternates between nonexistent (minimum, FeO2 0%) and the value according to the expiratory oxygen measurement of the patient (maximum, FeO2 100%). Assigning other indicators different in design to the ones described here as an embodiment of the disclosure will occur to those skilled in the art and may be used without varying from the spirit of this disclosure, e.g., using the display of more or fewer expired oxygen gas bubbles to indicate the value of the FeO2. A schematic overview of this algorithm is given in FIG. 33. FIG. 34 provides a graphical example of a change in volume or area of parts (3D) or area (2D) of the specific section 19 of region 6 according to different measurements of expired oxygen. Here, FIG. 34 shows graphical examples of a change in area[2D]/volume [3D] of the colored sections in part 6 according to expiratory oxygen data changes. A: expiratory oxygen of 16%, B: expiratory oxygen of 90%.

Example 16: Visual Patient Monitoring Algorithm #16 (Visual Brain Activity)

This algorithm allows both eyes of part 7 (e.g. FIG. 1) of the homunculus 10 to change their state, and the specific section of body 1 of the homunculus 10, representing the head 1*b* to indicate brain activity in an intuitive way according to a brain activity measurement, e.g., from the Bispectral index system (BIS) or an electroencephalography (EEG). Here, the patient monitoring quantity (inputs) is the Brain activity from e.g. the Bispectral Index system (BIS) or an Electroencephalography (EEG).

According to the value of the Bispectral index (BIS) or electroencephalography (EEG) data input the state of both eyes 7 changes from closed 7*b* to open 7*a*. The degree of openness will allow the user intuitively to understand the deepness of anesthesia of the patient P. Brain activity input indicative of deep anesthesia lead to eyes with eyelids closed (7*b*), values representing high brain activity indicating shallow anesthesia depth cause partially open (7*c*) eyes or eyelids 7 or open (7*a*) eyes 7.

Also, according to the BIS or EEG data input brain activity indicators appear around the section of region 1 of the homunculus 10 representing the head 1*b* of the visual patient monitoring. The amount of brain activity indicators presented allows the user intuitively to understand the brain activity of the patient (which is an indicator of anesthesia depth). Brain activity indicators for brain activity levels may be represented by dynamic waveform patterns, circles and stars rotating around and moving outwards and inwards in random movement from region 8 of the homunculus 10, representing the brain 8 of the homunculus located in head 1*b* of the homunculus 10.

Figure 35:
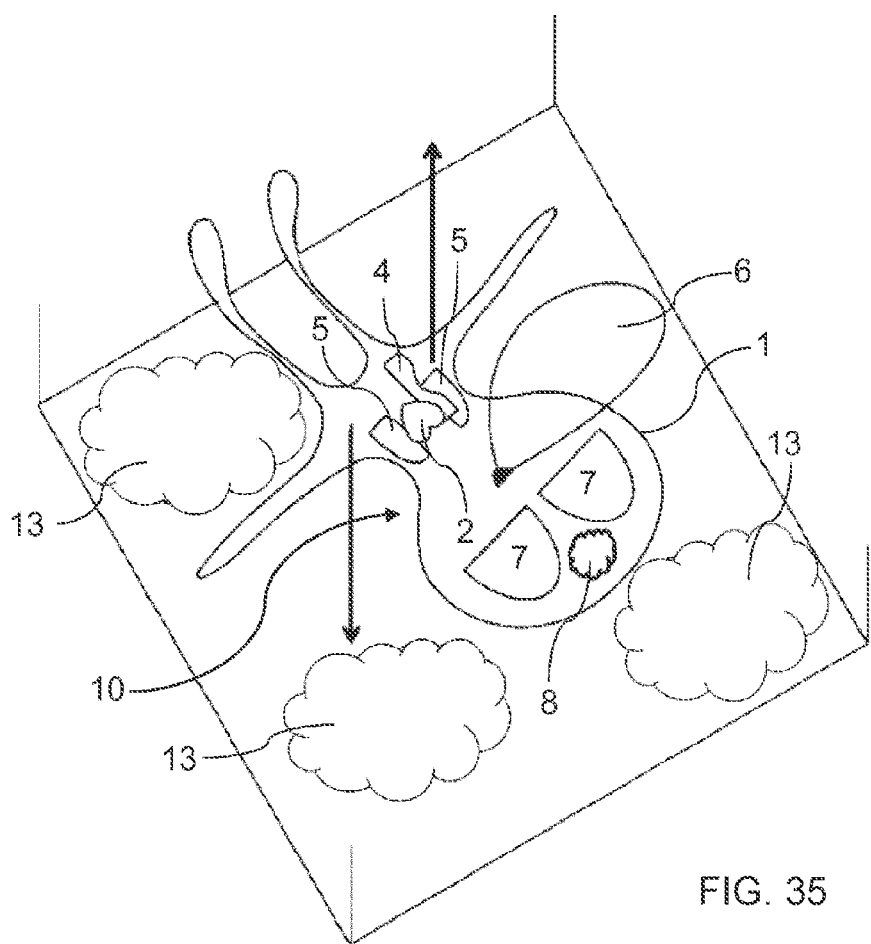
FIG. 35 is an illustration of graphical examples of how the homunculus may sink into or rise from a pool of liquid or clouds to represent depth of anesthesia as indicated by brain activity measurement.

They may be complemented by periodic nodding of the region 1*b* of body 1 representing the head, as well as yawning represented as opening of the mouth or grimacing of the homunculus appearing in prespecified ranges of brain activity. Also, the homunculus 10 may gradually be lowered into a pool of liquid or clouds to represent anesthesia, a graphical example of which is depicted in FIG. 35.

The degree of openness of the eyes 7 and the amount of brain activity indicators displayed, particularly follow an ease in/out function. This enables users better to detect low and high brain activity value extremes.

Assigning other designs to indicate anesthesia depth as described here as an embodiment of the disclosure will occur to those skilled in the art and may be used without varying from the spirit of this disclosure.

Figure 36:
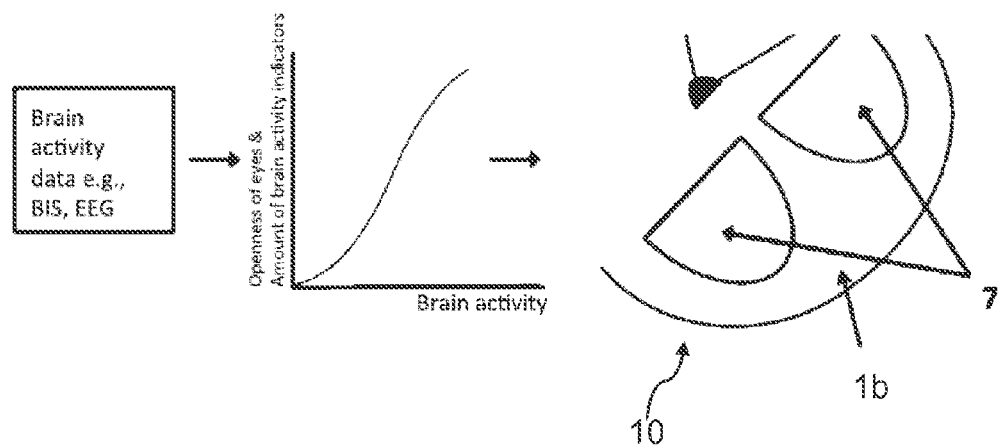
FIG. 36 is an illustration of a schematic overview of the logic of the visual patient monitoring algorithm #16 (visual brain activity).
Figure 37:
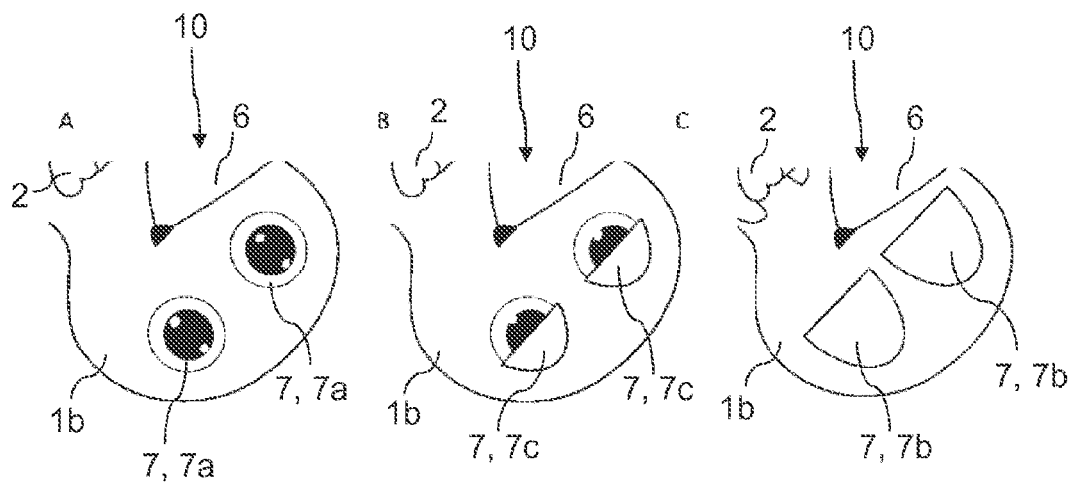
FIG. 37 is an illustration of graphical examples of the changes in the states of the eyes of the homunculus according to brain activity measurement.
Figure 38:
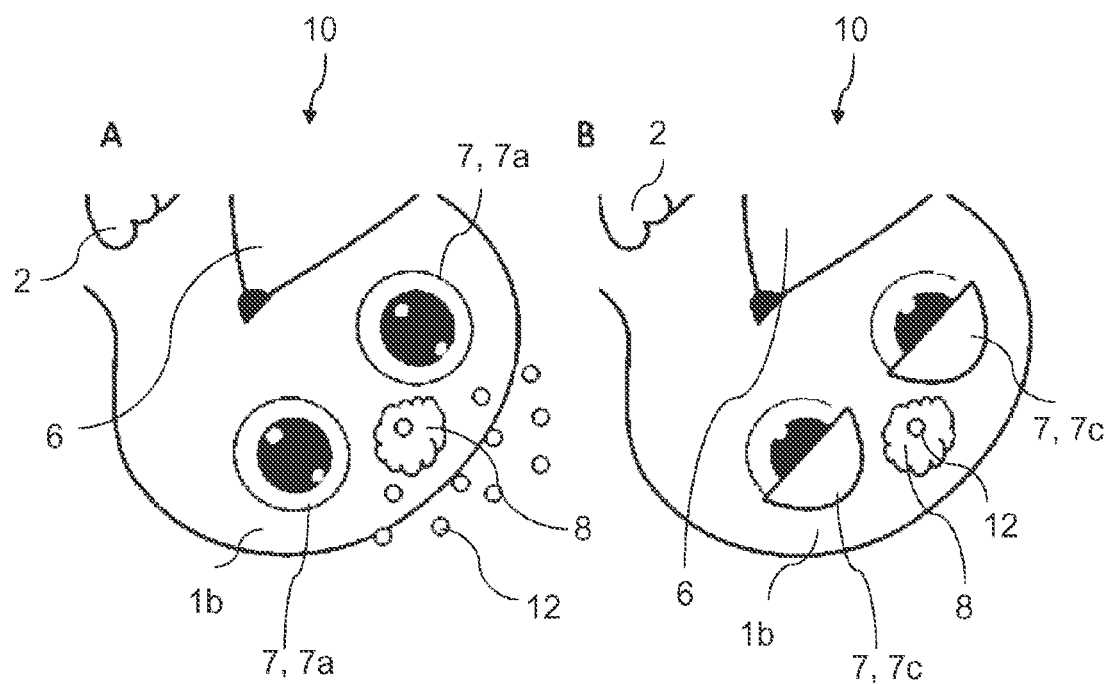
FIG. 38 is an illustration of graphical examples of the changes in the amount of brain activity indicators around part 1 of the homunculus measurement.

FIG. 36 gives a schematic overview of this algorithm. FIG. 37 provides a graphical example of a change in the state of both eyes 7 of the homunculus 10 according to the brain activity values. Here, FIG. 37 shows graphical examples of the changes in the states of both eyes 7 of the homunculus 10 according to changes in brain activity measurements (e.g., BIS, EEG). A: Eyes 7 in an open state 7*a* indicating a high brain activity, e.g., BIS 100, B: Eyes 7 in a partially open state 7*c* indicating medium brain activity, e.g., BIS value of 75, C: Eyes 7 in a closed state 7*b* indicating a low brain activity, e.g., BIS value of 40. Further, FIG. 38 shows graphical examples of the changes in the amount of brain activity indicators 12 displayed around or adjacent region 8 of the homunculus 10 representing the brain according to changes in brain activity measurements (e.g., BIS, EEG). A: High brain activity, e.g., BIS value of 100, B: low brain activity, e.g., BIS value of 40.

Example 17: Visual Patient Monitoring Algorithm #17 (Visual Intracranial Pressure)

This algorithm allows region 8 (FIG. 1) of the homunculus 10 forming the brain to change its volume or area of parts (3D) or area (2D) and appearance in an intuitive way according to the intracranial pressure of the patient P. Here, the patient monitoring quantity (input) is the intracranial pressure (ICP).

Figure 39:
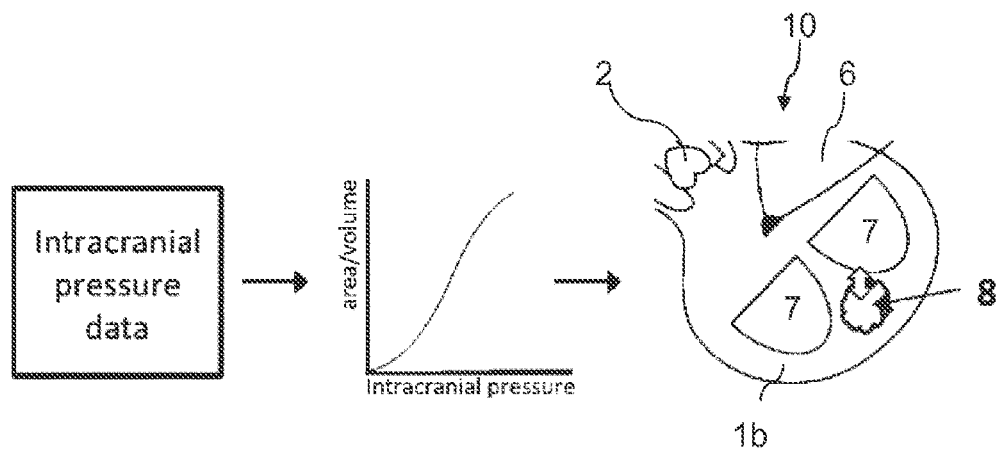
FIG. 39 is an illustration of a schematic overview of the logic of the visual patient monitoring algorithm #17 (visual intracranial pressure).
Figure 40:
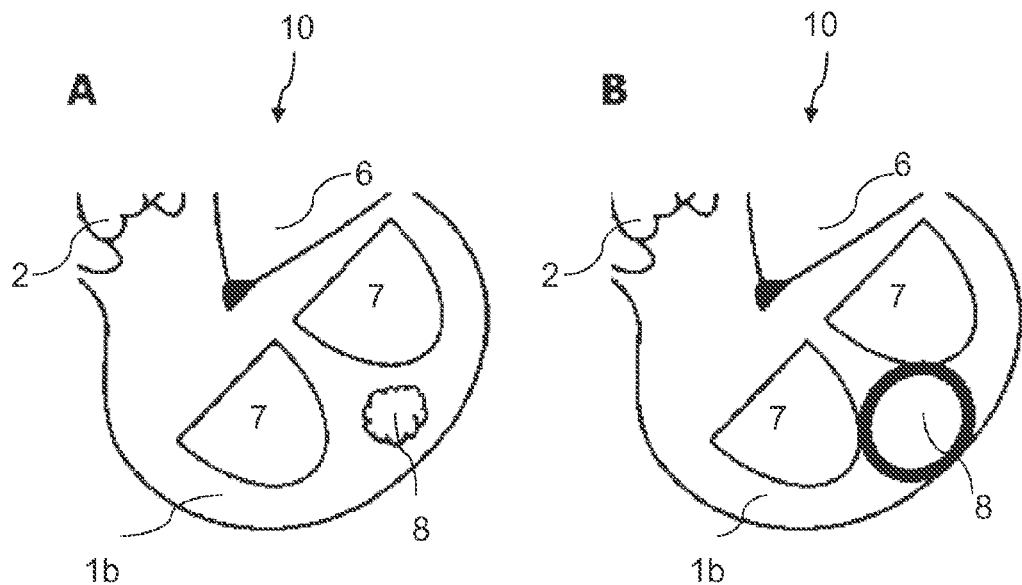
FIG. 40 is an illustration of graphical examples of the changes in the appearance of part 8 of the homunculus according to intracranial pressure data.

Changes in input intracranial pressure lead to a change in volume or area of parts (3D) or area (2D) of brain 8 particularly following an ease in/out function. Also, the appearance of region 8 will gradually change according to an ease in/out function from an appearance where the brain 8 appears relaxed to an appearance where the brain 8 appears compressed and tense, representing high intracranial pressure. The ease in/out functions causes very low and very high pressures to cause less extensive changes in volume or area of parts (3D) or area (2D) of region 8 when compared to changes in medium pressure ranges. This function will enable users better to detect low and high extremes of intracranial pressure. The volume or area of parts (3D) or area (2D) of region (i.e. brain) 8 of the homunculus 10 fluctuate according to the ICP pressure wave, when this input is available. Assigning other designs to indicate intracranial pressure then described here as an embodiment of the disclosure will occur to those skilled in the art and may be used without varying from the spirit of this disclosure. FIG. 39 provides a schematic overview of this algorithm. FIG. 40 provides a graphical example of a change in the appearance of brain 8 of the homunculus 10 according to different measurements of intracranial pressure. Here, FIG. 40 shows a graphical example of a change in the appearance of brain 8 of the homunculus according to changes in intracranial pressure measurements. A: A normal ICP, the sulci of the brain 8 are visible B: high ICP, the brains 8 gyri and sulci are no longer visible. The brain 8 appears compressed.

Example 18: Visual Patient Monitoring Algorithm #18 (Visual Brain Tissue Oxygen Tension)

This algorithm allows region (i.e. brain) 8 of the homunculus (e.g. FIG. 1) to change its color in an intuitive way according to the brain tissue oxygen tension of the patient. Here, the patient monitoring quantity (input) is the brain tissue oxygen tension (BO).

Changes in brain tissue oxygen tension lead to a change in color of brain 8 of the homunculus 10. At 100% oxygen saturation brain 8 of the homunculus 10 has a normal white color, representing well-oxygenated brain tissue. As oxygen content decreases the color gradually turns from a light blue color (e.g., HEX color #84B0E8) to a darker blue (e.g., HEX color #0E3996) and eventually turns purple (e.g., HEX color #723C7F) and dark grey (e.g., HEX color #DEDEDE) representing various degrees of brain tissue hypoxia. Assigning other, different colors to the central venous saturation data points will occur to those skilled in the art and may be used without varying from the spirit of this disclosure.

The changes in color from normal white to dark blue and eventually grey follow an ease in/out function. This function will enable users better to detect low and high brain tissue oxygen tension extremes.

Figure 41:
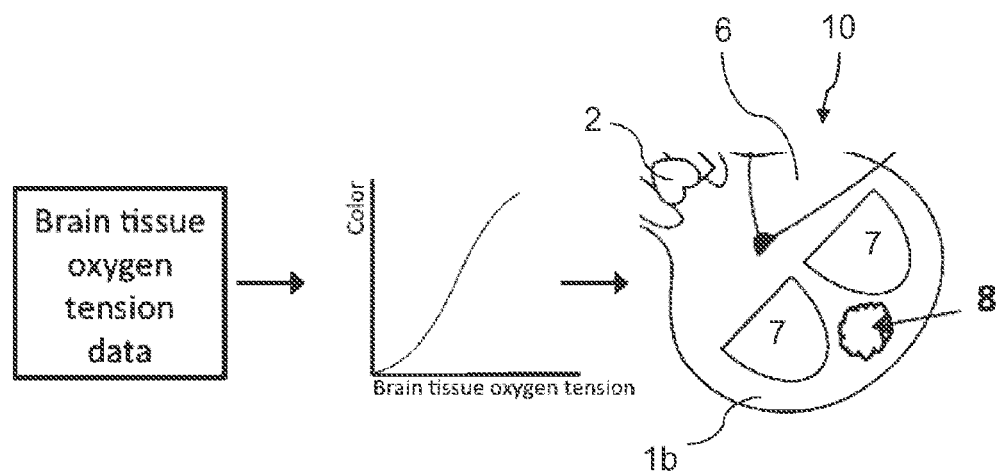
FIG. 41 is an illustration of a schematic overview of the logic of the visual patient monitoring algorithm #18 (visual brain tissue oxygen tension).
Figure 42:
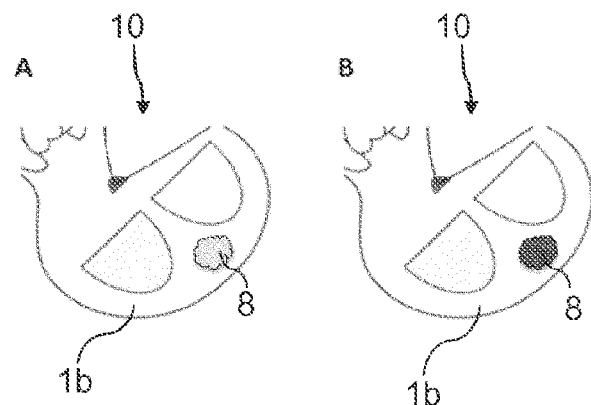
FIG. 42 is an illustration of graphical examples of the changes in color of part 8 of the homunculus according to brain tissue oxygen tension.

FIG. 41 gives a schematic overview of this algorithm. FIG. 42 provides a graphical example of a color change (indicated in grey scale) of the region (i.e. brain) 8 of the homunculus 10 according to brain tissue oxygen saturation measurements. Particularly, FIG. 42 shows a graphical example of a change in color (indicated in grey scale) of brain 8 of the homunculus 10 according to brain tissue oxygen saturation. A: 100% oxygen saturation, B: 75% oxygen saturation.

Example 19: Visual Patient Monitoring Algorithm #19 (Visual Neuromuscular Transmission)

This algorithm allows the body 1 and both hands 9 (particularly also thumbs 9a) of the homunculus 10 (e.g. FIG. 1) to change their state in an intuitive way according to the neuromuscular transmission measurement system (NMT). Here, the patient monitoring quantity (input) is provided e.g. by a neuromuscular transmission measurement system (NMT).

According to the value of the neuromuscular transmission measurement (NMT) data input, the body 1, hands 9 and thumbs 9a of the homunculus 10 change from relaxed (flaccid) to tense and the hands 9 show an extended thumb (thumbs up) 9a. The degree of relaxation of the hands and extension of the thumb will allow the user intuitively to understand the degree of neuromuscular transmission of the patient. NMT values indicative of good muscle relaxation lead to the fingers of the hands and all joints to hang down giving a relaxed indication. High NMT values, indicating good neuromuscular transmission, cause the hand to tighten and the thumbs on the hands to extend.

Also, according to the NMT data input part 1 of the homunculus may change its shape to appear tilted at the knees and the elbows to represent muscle weakness or muscle strength intuitively. NMT values indicative of good muscle relaxation lead to changes in the relative positions of the sections of part 1 of the homunculus representing the legs, arms and head, giving a relaxed indication. They appear to hang down following the gravitational force. High NMT values, indicating good neuromuscular transmission, cause the legs and arms to appear tense.

Figure 43:
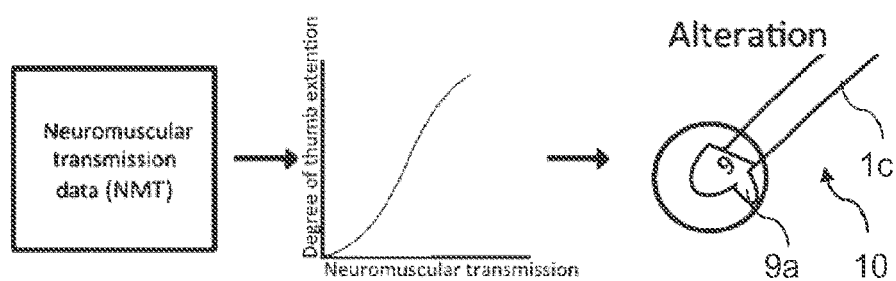
FIG. 43 is an illustration of a schematic overview of the logic of the visual patient monitoring algorithm #19 (neuromuscular transmission measurement system data).

The degree of relaxation of the hands and extension of the thumb follows an ease in/out function. This enables users better to detect low and high NMT value extremes. Assigning other ways than described here an embodiment will occur to those skilled in the art and may be used without varying from the spirit of this disclosure. FIG. 43 gives a schematic overview of this algorithm. FIG. 44 provides graphical examples of the changes according to different NMT measurements. Here, FIG. 44 shows graphical examples of the changes to the stiffness of arms, legs and neck according to different NMT measurements. A: no relaxation e.g., TOF ratio 100%, B: deep relaxation e.g., TOF ratio 0%, Count 0.

The general visual patient monitoring algorithm (FIG. 6), the subroutines (FIGS. 8 and 9) and algorithms #1 to #19 of the present disclosure are embodied in software or code executed by general purpose hardware as discussed above. As an alternative, the algorithms and subroutines may also be embodied in dedicated hardware or a combination of software/general purpose hardware and dedicated hardware. If embodied in dedicated hardware, the algorithms and subroutines can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, programmable gate arrays (PGA), field programmable gate arrays (FPGA), or other components, etc. Such technologies are well known by those skilled in the art and, consequently, are not described in detail herein.

The algorithms and subroutines illustrate the architecture, functionality, and operation of an implementation of the disclosure. If embodied in software, each block may represent a module, segment or portion of code that comprises program instructions to implement the specified logical function(s). The program instructions may be embodied in the form of source code that comprises human-readable statements written in a programming language or machine code that comprises numerical instructions recognizable by a suitable execution system such as a processor in a computer system or other system. The machine code may be converted from the source code, etc. If embodied in hardware, each block may represent a circuit or a number of interconnected circuits to implement the specified logical function(s).

Although the algorithms and subroutines show a specific order of execution, it is understood that the order of execution may differ from that which is depicted. For example, the order of execution of two or more blocks may be scrambled relatively to the order shown. Also, two or more blocks shown in succession in the algorithms and subroutines may be executed concurrently or with partial concurrence. In addition, any number of numerals, waveforms, state variables, data buffers, warning semaphores, or messages might be added to the logical flow described herein, for purposes of enhanced utility, accounting, performance measurement, or providing troubleshooting aids, etc. It is understood that all such variations are within the scope of the present disclosure. Also, the block diagrams, flow charts and graphics are relatively self-explanatory and are understood by those with ordinary skill in the art to the extent that software and/or hardware can be created by one with ordinary skill in the art to carry out the various logical functions as described herein.

Where the algorithms and subroutines comprise software or code, it can be embodied in any computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the algorithms and subroutines for use by or in connection with the instruction execution system. The computer readable medium can comprise any one of many physical media such as, for example, electronic, magnetic, optical, electromagnetic, infrared, or semiconductor media. More specific examples of a suitable computer-readable medium would include but are not limited to, magnetic tapes, magnetic floppy diskettes, magnetic hard drives, flash memory, or compact discs. Also, the computer-readable medium may be a random access memory (RAM) including, for example, static random access memory (SRAM) and dynamic random access memory (DRAM), magnetic random access memory (MRAM), or non-volatile random-access memory (NVRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Although the disclosure has been shown and described with respect to certain preferred embodiments, equivalent alterations and modifications will occur to those skilled in the art upon reading and understanding this specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function of the described integer (i.e., that is functionally equivalent), even though not structurally equivalent to the disclosed structure which performs the function in the herein illustrated exemplary embodiment or embodiments of the disclosure. In addition, while a particular feature of the disclosure may have been described above with respect to only one of several illustrated embodiments, such feature may be combined with one or more other features of the other embodiments, as may be desired or advantageous for any given or particular application.

Figure 45B:
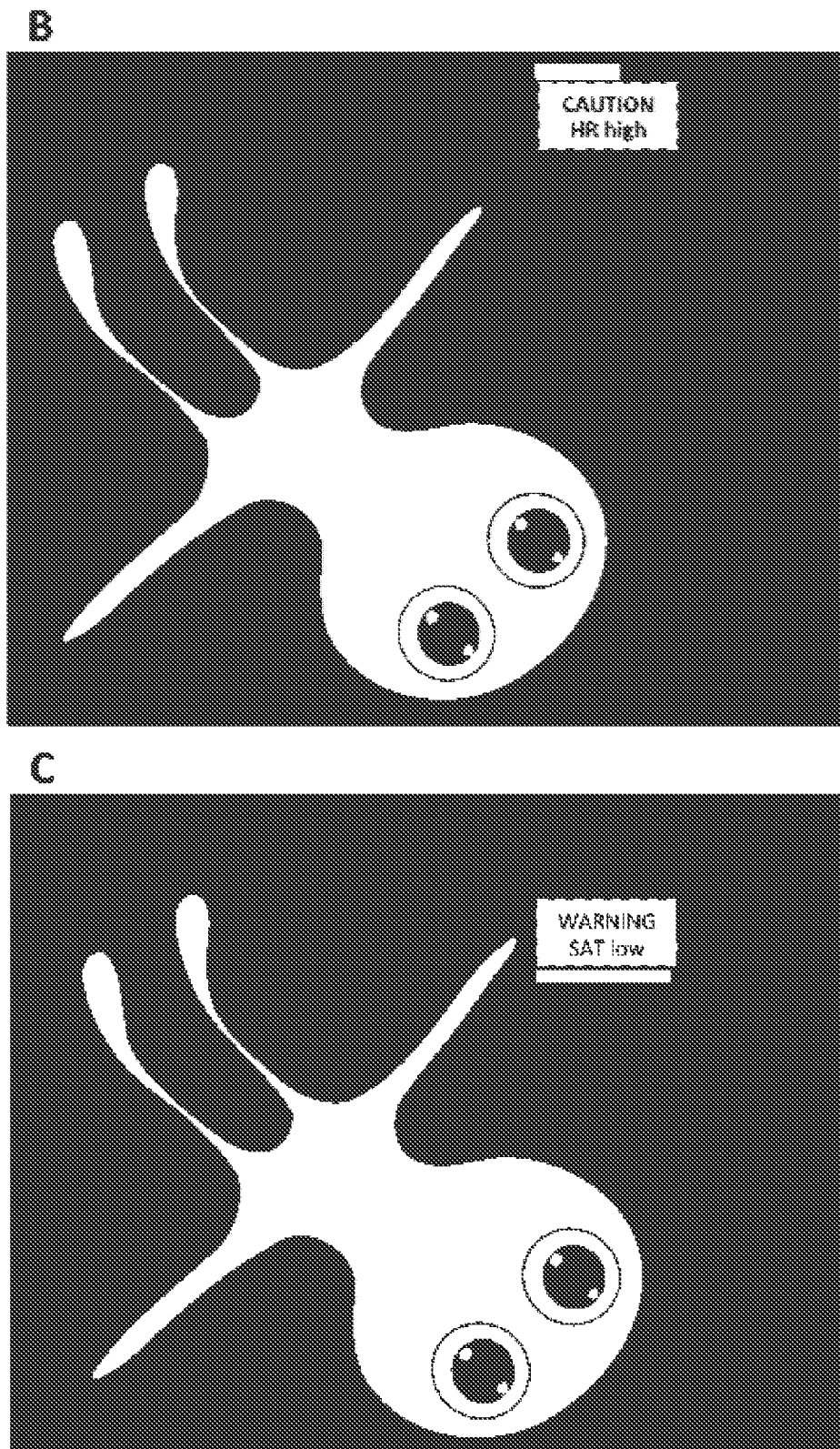
Figure 45C:
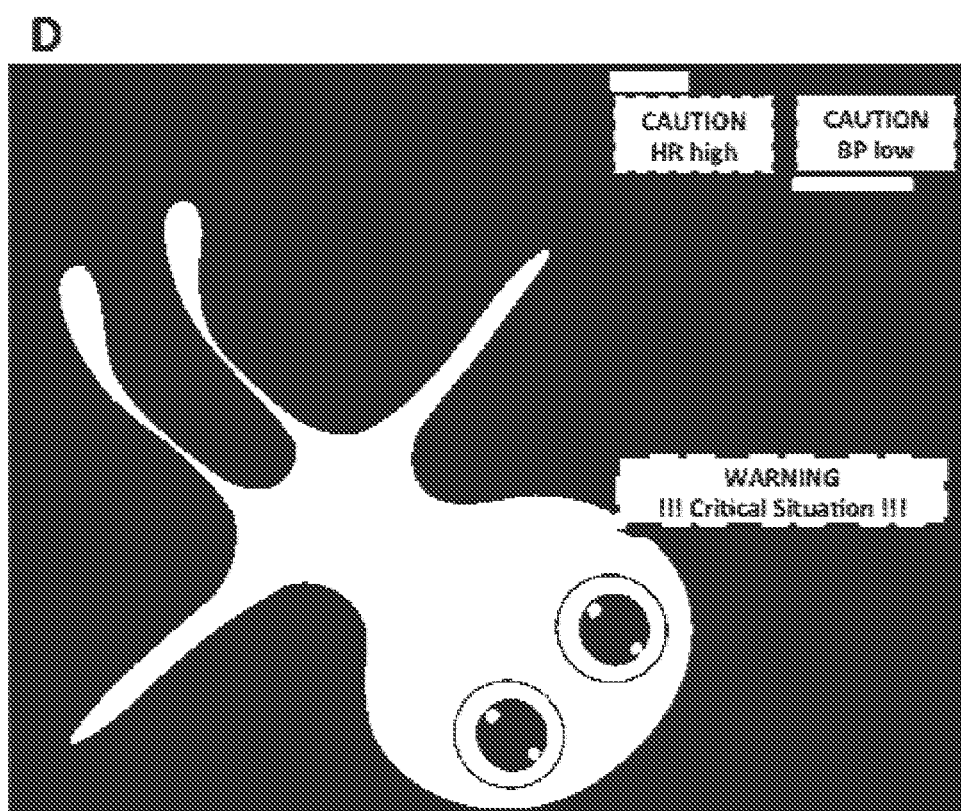

An example of how warning semaphores is implemented as part of an embodiment of the disclosure is through the use of an alarm system representing an annunciator panel. Accompanying the graphical homunculus display (or instrument) could be a panel displaying alerts showing fields with the designations of the monitored parameters in a specific order and place, as in an annunciator panel. The order of the fields and the normal range of the parameters may be configurable by the user or may be dynamically adapted by the software. When the measured value of a parameter is within its normal range, its corresponding field is invisible, i.e., not displayed. FIGS. 45A, 45B and 45C show graphical examples of how the described alarm system may be implemented in an embodiment of the disclosure.

Figure 46:
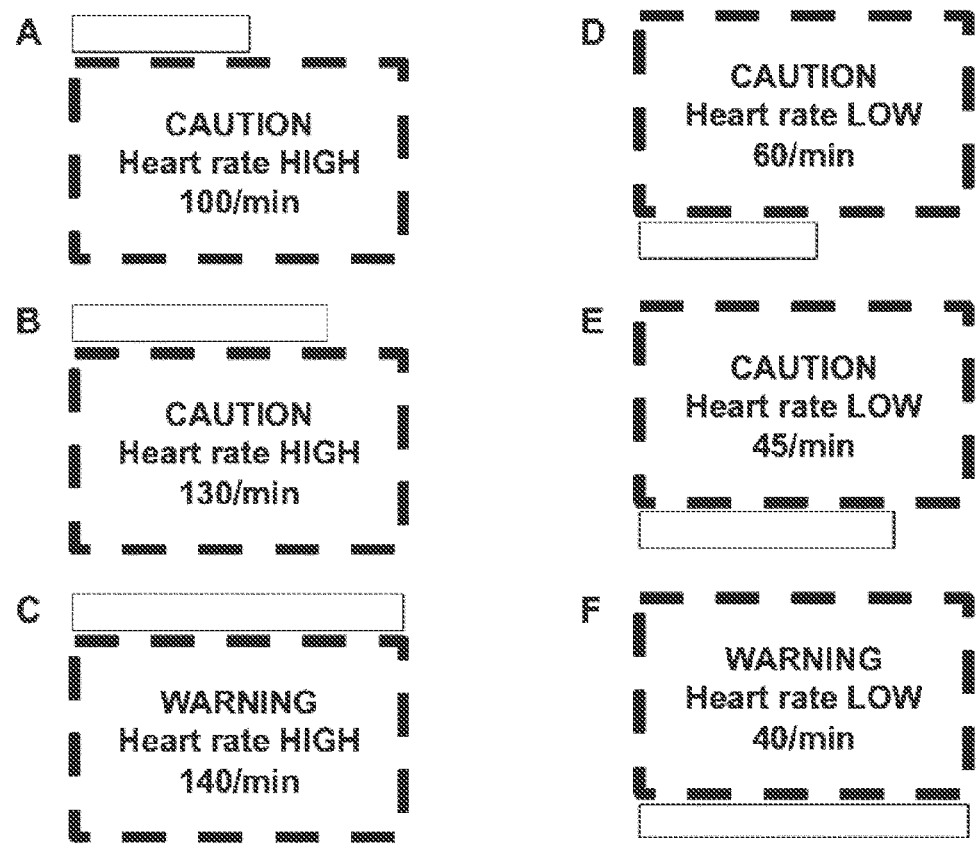
FIG. 46 is an illustration of graphical examples of how various "CAUTION" and "WARNING" states could be displayed according to an embodiment of the disclosure.

According to predefined abnormal ranges, an abnormal measurement for a parameter may cause the field displaying the name of the abnormal parameter to become visible and turn yellow, i.e., to signify a state that requires CAUTION, or red, i.e., to indicate a WARNING of a dangerous state. In an embodiment, these alerts may be accompanied by a bar in the correspondent color (yellow or red), with the length of the colored bar indicating the magnitude of deviation from the normal, and the position of the bar on the upper or lower border of the field indicating a deviation above (upper border) or below (lower border) the normal range. When the measured value of a parameter reaches a value in the defined CAUTION range, the colored yellow bar spans over half of the fields upper or lower border (50%). When a measured value of a parameter reaches a value halfway between the value defined as the beginning of the CAUTION range and the value defined as the beginning of the WARNING range, the length of the yellow bar will gradually increase with the value of the measured parameter from 50% to 100%. FIG. 46 shows graphical examples of fields showing various CAUTION and WARNINGS states.

Additionally, the volume or area of parts (3D) or area (2D) or length representing the abnormal parameter in the visual patient display (or instrument) may alternate its color between the color displayed by the visual patient graphical display and the abnormal yellow or red color, e.g. in 1 second intervals. Combinations of two or more specified parameters in the CAUTION range will produce a WARNING and cause the display of an additional critical situations alert, indicating to the user that a dangerous situation may be occurring. A graphical example of this is shown in FIG. 45C (D). Table 2 (page 46) outlines examples of parameter combinations, which will cause the display of a critical situation alert, when in an abnormal range at the same time.

In detail, FIGS. 45A, 45B, and 45C show graphical examples A, B, C, and D of how an alarm system based on caution and warning fields and color changes of the part of the homunculus representing the abnormal parameter may be implemented. Example A: All parameters are in the normal range; the fields for the cautions or warnings are invisible. This is a "no caution no warning" situation. In the example of picture A, for illustrating purposes, fields are shown in transparent to illustrate the arrangement like an annunciator panel. Example B: The parameter heart rate is above its normal range. A yellow caution appears with arrows pointing upwards and region (i.e. heart) 2 of the homunculus 10 intermittently flashes yellow. Example C: The parameter oxygen saturation is far below its normal range, a red warning sign with arrows pointing downwards appears and region (i.e. body) 1 of the homunculus 10 intermittently flashes red. Example D: The parameters heart rate is above and the parameter blood pressure is below its normal range. In addition to the yellow caution signs for the two parameters, a critical situation alert appears.

Further, in detail, FIG. 46 shows graphical examples of various "CAUTION" and "WARNING" states. A: The measured value for heart rate is high (100/min) and within the range defined as "CAUTION". B: The measured value for heart rate is high (130/min) and between the value defined as the beginning of the "CAUTION" range (100/min in this example) and the value defined as the beginning of the "WARNING" range (140/min in this example). The bar at the top of the field has increased to a length of 75% of the field. C: The measured value for heart rate is high (140/min) and within the range defined as "WARNING". D: The measured value for heart rate is low (60/min) and within the range defined as "CAUTION". E: The measured value for heart rate is low (45/min) and between the value defined as the beginning of the "CAUTION" range (60/min in this example) and the value defined as the beginning of the "WARNING" range (40/min in this example). The bar at the bottom of the field has increased to a length of 75% of the field. F: The measured value for heart rate is high (40/min) and within the range defined as "WARNING".

Critical Situation Alarm System

Table 2 outlines examples of combinations of parameters, which, when in an abnormal range will cause the display of an additional critical situation alert ("WARNING") according to an embodiment of the disclosure.

|  | above (↑) normal range | below (↓) normal range |
| --- | --- | --- |
| Blood pressure (BP) | BIS ↑ | Pulse rate ↑, ECG QRS Heart rate ↑ |
|  |  | Intracranial pressure ↑ |
| Pulse Rate SpO2 Sensor (PR) | Blood pressure (BP) ↓ | SaO2 ↓ |
| Oxygen saturation (SpO2) | (none) | Tidal volume ↓, Respiratory rate ↓, Expiratory oxygen measurement ↓, Brain tissue oxygen tension ↓ Blood pressure (BP) ↓ |
| Body Temperature (Temp) | eCO2 ↑ (-> MH!) | ECG QRS Heart rate ↓ |
| ECG QRS Heart Rate (HR) | Blood pressure (BP) ↓ | Blood pressure (BP) ↓ |
| ECG ST-segment deflection (ST) |  |  |
| ECG rhythm detection (ECG) |  |  |
| Right ventricular pressure (RVP) | eCO2 ↑ SaO2 ↓ | Blood pressure (BP) ↓ |
| Pulmonary capillary wedge pressure or wedge pressure (PCWP) | Blood pressure (BP) ↓ CO/CI ↓ | Blood pressure (BP) ↓ |
| Mixed venous oxygen saturation (MVOS) |  | CO/CI ↓ |
| Central venous pressure (CVP) | Blood pressure (BP) ↓ CO/CI ↓ | ECG QRS Heart rate ↑ |
| Respiratory rate (RR) |  | Oxygen saturation ↓, Tidal volume ↓, Expiratory oxygen measurement ↓, Brain tissue oxygen tension↓ |
| Tidal volume (TV) |  | Oxygen saturation ↓, Respiratory rate ↓, Expiratory oxygen measurement ↓, Brain tissue oxygen tension↓ |
| exspiratory carbon dioxide (eCO2) | Tidal volume ↓, Respiratory rate ↓ |  |
| Expiratory oxygen measurement (eO2) |  | Oxygen saturation ↓, Tidal volume ↓, Respiratory rate ↓, Brain tissue oxygen tension↓ |
| Brain activity from e.g., Bispectral Index System (BIS), electroencephalogram (EEG) | Neuromuscular transmission measurement system ↓ |  |
| Intracranial pressure | Blood pressure ↓ |  |
| Brain tissue oxygen tension |  | Oxygen saturation ↓, Expiratory oxygen measurement ↓, Tidal volume ↓, Respiratory rate |
| Neuromuscular transmission measurement system (NMT) |  | Brain activity ↑ |

What is claimed is:

1. A method for monitoring a medical state of a patient through a dynamically rendered visualization of a synthetic two or three dimensional patient model, the monitoring involving monitoring one or more medical parameters of the patient, the patient model representing the medical state of the monitored patient and being rendered into a graphical representation of the patient over a range of values of a specific monitored medical parameter of the patient, the method comprising:

a group of algorithms including:

a first patient monitoring algorithm, wherein a volume of a rendered region corresponding to the patient's vena cava region is associated with a current value of the patient's mean central venous pressure (CVP), wherein the volume of the patient's vena cava region is re-rendered when the current value of the patient's mean central venous pressure (CVP) changes, and wherein the volume of the patient's vena cava region is proportional to the current value of the patient's mean central venous pressure (CVP);

a second patient monitoring algorithm, wherein a volume of a rendered region corresponding to the patient's lung is altered between a first value and a second value derived from a tidal volume (TV), respectively, with a display refresh frequency associated with a respiratory rate (RR), and wherein the first value is smaller than the second value;

a third patient monitoring algorithm, wherein a volume of a rendered region corresponding to the patient's expiratory CO2 cloud is altered between a first value and a second value derived from a capnographic value (CAP), respectively, with the display refresh frequency being associated with the patient's respiratory rate (RR), and wherein the first value is smaller than the second value;

a fourth patient monitoring algorithm, wherein a rendered region corresponding to the patient's eye is altered when a bispectral index (BI) value changes, wherein when the index (BI) lies in a first range, the patient's eye region is rendered in an open state, and wherein when the index (BI) lies in a second range, the patient's eye region is rendered in a closed state, and wherein when the index (BI) is in a third range, the patient's the eye region is rendered in a partially open state; and a fifth patient monitoring algorithm, wherein a rendered region corresponding to the patient's hand is altered when a current neuromuscular transmission (NMT) value changes, wherein when the current neuromuscular transmission (NMT) value lies in a first range, the patient's hand region is rendered in a first state, in a relaxed state, and wherein when the current neuromuscular transmission (NMT) value lies in a second range, the patient's hand region is rendered in a different second state with an extended thumb and tightened fingers; and re-rendering the graphical representation of the monitored patient in response to changes in the monitored patient's medical state according to at least one algorithm selected from the group of algorithms, wherein the re-rendering of the graphical representation occurs at a pre-defined display refresh frequency that is associated with medical state value ranges of corresponding real-time parameters monitored by the selected algorithm, and wherein changes in the re-rendering frequency of each rendered region in the graphical representation of the monitored patient, for the selected algorithm, occurs only when a corresponding monitored parameter value crosses a pre-defined threshold value that is indicative of change in the monitored patient's medical state.

2. The method of claim 1, wherein in the re-rendered graphical representation, a change in a volume and/or appearance of at least one region of the graphical representation is displayed using a non-linear smoothing function, the non-linear smoothing function providing smooth visual changes in the volume and/or appearance of the at least one region at low ends of the range of values and at high ends of the range of values of the specific monitored medical parameter of the patient, and wherein the non-linear smoothing function is a monotonically increasing function that is convex for a first part of the range of values of the specific monitored medical parameter of the patient and concave for a succeeding second part of the range of values of the specific monitored medical parameter of the patient.

3. The method of claim 2, wherein the smoothing function is:

$$f(x)=(\sin(\pi^*x/x_{max}-\pi/2)+1)^*y_{max}/2,$$

where x is the specific monitored medical parameter of the patient within the interval $[0; x_{max}]$ and $y_{max}$ is a maximum value of the specific monitored medical parameter of the patient.

4. The method of claim 1, wherein the re-rendering the graphical representation of the patient in response to changes in the monitored patient's medical state includes:

rendering and re-rendering a cloud visualization that reflects a gas composition measured in the patient's breath, wherein a volume or area of the cloud visualization alternates in size between a maximum and minimum expiratory carbon dioxide concentration value measured during a breath cycle, wherein a frequency of the alternation between minimum and maximum is proportional to the respiratory rate of the patient.

5. The method of claim 1, wherein the re-rendering the graphical representation of the patient in response to changes in the monitored patient's medical state includes:

rendering and re-rendering a visualization indicative of the patient's anesthesia depth.

6. The method of claim 1, wherein the re-rendering the graphical representation of the patient in response to changes in the monitored patient's medical state includes:

rendering a form of the patient model's body based on a measured neuromuscular transmission value, the form including the extended thumb and tightened fingers when the neuromuscular transmission value is in a normal range, and the form including the patient's extremities hanging down to represent the effect of gravity on the patient with impaired neuromuscular transmission.

7. The method of claim 1, wherein the group of algorithms further includes: a sixth patient monitoring algorithm, wherein a volume of a rendered region corresponding to the patient's heart is changed between a first value derived from a current diastolic blood pressure (DBP) and a second value derived from a current systolic blood pressure (SBP), wherein the first value is smaller than the second value, and wherein the display refresh frequency for re-rendering the rendered region corresponding to the patient's heart is associated with an electrocardiogram (ECG) QRS heart rate (HR) of the monitored patient; and a seventh patient monitoring algorithm, wherein the rendered region corresponding to the patient's heart is re-rendered with the display refresh frequency according to the patient's current ECG rhythm, the ECG rhythm being detected by an ECG rhythm detection system, and wherein re-rendering includes the insertion of a graphical indicator in the rendered region corresponding to the patient's heart, the graphical indicator being indicative of a type of the ECG rhythm.

8. A computer program product for monitoring the medical state of a patient, the computer program product comprising instructions embodied on a non-transitory computer readable medium, the instructions when executed by a processor cause the processor to implement the method of claim 1.

9. A system for monitoring and visualizing a patient's medical condition, wherein the system comprises a central processing unit, a memory, a graphics processor and a display device and is configured to conduct the method of claim 1.

* * * * *